United States Patent
Kelly et al.

(10) Patent No.: US 8,150,711 B2
(45) Date of Patent: Apr. 3, 2012

(54) GENERATING AND MANAGING MEDICAL DOCUMENTATION SETS

(75) Inventors: Lisa Kelly, Overland Park, KS (US); Mary Gannon, Shawnee, KS (US); Martha Gerling, Kansas City, MO (US); Stephanie Rogers, Kansas City, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 395 days.

(21) Appl. No.: 12/244,439

(22) Filed: Oct. 2, 2008

(65) Prior Publication Data
US 2009/0094061 A1    Apr. 9, 2009

Related U.S. Application Data

(60) Provisional application No. 60/977,985, filed on Oct. 5, 2007.

(51) Int. Cl.
G06F 19/00    (2011.01)

(52) U.S. Cl. .......................................................... 705/3

(58) Field of Classification Search .................. 705/2, 3; 128/920
See application file for complete search history.

(56) References Cited

U.S. PATENT DOCUMENTS

| 6,026,363 | A  * | 2/2000  | Shepard ........................... 705/3 |
| 2002/0170565 | A1 * | 11/2002 | Walker et al. .................. 128/920 |
| 2004/0172306 | A1 * | 9/2004  | Wohl et al. ......................... 705/3 |
| 2005/0027569 | A1 * | 2/2005  | Gollogly et al. .................. 705/3 |

* cited by examiner

*Primary Examiner* — Gerald J. O'Connor
*Assistant Examiner* — John Pauls
(74) *Attorney, Agent, or Firm* — Shook, Hardy & Bacon L.L.P.

(57) ABSTRACT

Methods, computer storage media, systems and user interfaces for generating and/or managing medical documentation sets are provided. Medical documentation sets are generated by replicating a predetermined medical template. After the predetermined medical template is replicated, the medical label associated with the medical documentation set may be modified so that the medication documentation set includes a unique medical label. Upon the completion of a medication documentation set, it may be retrieved and managed as desired.

20 Claims, 19 Drawing Sheets

| | SEPTEMBER 16, 2007 7:00 AM – SEPTEMBER 19, 2007 6:59 AM | | | |
|---|---|---|---|---|
| | TODAY'S INTAKE: 0 OUTPUT: 130 BALANCE: -130  YESTERDAY'S INTAKE: OUTPUT: BALANCE: | | | |
| | 9/17/2007 | | | |
| | 1:00 PM – 1:59 PM | 12:00 PM – 12:59 PM | 11:00 AM – 11:59 AM | 10:00 AM – 10:59 AM |
| ⊟ INTAKE TOTAL | | | | |
| ⊞ TEST RG IO2 | | | | |
| ⊟ OUTPUT TOTAL | | 130 | | |
| ⊞ STOOL OUTPUT | | | | |
| ⊟ DRAINS AND TUBES IO | | | | |
| ⊞ LEFT LOWER ABDOMEN P... | | | | |
| ⊞ RIGHT UPPER LEG JP | | | | |
| ⊞ LE 1302 K WITH INCISION — 1304 | | | | |
| ⊞ Rlgl LOWER ABDOMEN JP | | | | |
| ⊟ <DRAIN LATERALITY><DRAIN LOC... | | | | |
| DRAINAGE VOLUME  ML | | | | |
| DRAINAGE DESCRIPTION | | | | |
| ⊞ CHEST TUBE OUTPUT IO | | 130 | | |
| BALANCE | | -130 | | |

*(Screen capture of a medical documentation interface showing RN View with Drains and Tubes documentation over the Last 24 Hours)*

| | | 1:00 PM - 1:59 PM | 12:00 PM - 12:59 PM | 11:00 AM - 11:59 AM | 10:00 AM - 10:59 AM |
|---|---|---|---|---|---|
| ☐ DRAINS AND TUBES | | | | | |
| ☐ LEFT LOWER ABDOMEN PENROSE | | | | | |
| DRAINAGE VOLUME | ML | | 60 | | |
| DRAINAGE DESCRIPTION | | | BLOODY, THIN | | |
| DRAIN TO SUCTION | | | NO | | |
| ☐ RIGHT UPPER LEG JP | | | | | |
| DRAINAGE VOLUME | ML | | 30 | | |
| DRAINAGE DESCRIPTION | | | SEROSANGUIN | | |
| DRAIN TO SUCTION | | | YES | | |
| ☐ LEFT NECK WITHIN INCISION JP | | | | | |
| DRAINAGE VOLUME | ML | | 20 | | |
| DRAINAGE DESCRIPTION | | | BLOODY, THIN | | |
| DRAIN TO SUCTION | | | YES | | |
| ☐ RIGHT LOWER ABDOMEN JP | | | | | |
| ☐ LEFT ARM WOUND VAC | | | | | |
| DRAINAGE VOLUME | ML | | 50 | | |
| RIGHT LOWER ABDOMEN JP | | | BLOODY | | |
| ☐ CHEST TUBES | | | | | |

Menu items (left panel): MATERNAL LABS, NASOGASTRIC, NON PRIMITIVE, NON PRIMITIVE1, O2/PULSE OX CHECK, OB/GYN ASSESSMENT, OSTOMY CARE SECTION, PAIN REASSESSMENT, SKIN ASSESSMENT, THYROID STUDIES, URINE OUTPUT, VITAL SIGNS, ✓ DRAINS AND TUBES, INTAKE AND OUTPUT, LAB RESULTS, MEDS, GRAPHS, GEN VIEW, TEST VIEW, VIEW, ICUVIEW1, IO TOTALS, ROSS' DEMO VIEW Labels: 1900, 1902, 1904

GENERATING AND MANAGING MEDICAL DOCUMENTATION SETS

CROSS-REFERENCE TO RELATED APPLICATIONS

This application claims the benefit of U.S. Provisional Patent Application No. 60/977,985, filed Oct. 5, 2007, entitled "Generating and Managing Medical Documentation Sets."

This application is related by subject matter to U.S. patent application Ser. No. 12/244,449 filed even date herewith and entitled "User Interface for Generating and Managing Medical Documentation Sets", which is assigned or under obligation of assignment to the same entity as this application, and incorporated in this application by reference.

BACKGROUND

Medical care in association with procedures, medications, laboratory tests, evaluations, treatments, and assessments performed for a patient is oftentimes electronically documented by healthcare providers. In an electronic healthcare environment, a documentation section for recording medical data associated with a specific medical event is established by a healthcare provider around the time of a medical event for which documentation is desired. Additional documentation sections are also established by the healthcare provider upon the occurrence of or in advance of subsequent medical events. Accordingly, the healthcare provider is required to independently create a documentation section for each medical event. That is, for each documentation section, the healthcare provide must specify the data elements desired to be included therein. As such, each documentation section might have varied data elements and/or a varied numbers of data elements even though the documentation sections are associated with a common medical category (e.g., drains and tubes). In addition, each documentation section is provided with a nonspecific label.

Such an individual creation of a documentation section is both time-consuming and error prone. For example, specifying data elements for inclusion within each new documentation section is inefficient in that it requires the healthcare provider to duplicate efforts in creating multiple documentation sections. In addition, such varied documentation sections can prevent or hinder the ability to group documentation sections, or portions thereof, and/or analyze or trend data provided within the documentation sections. Further, such nonspecific labels can provide confusion and even cause healthcare providers to commit errors in providing medical care.

Thus, it would be beneficial to have a system and method in an electronic healthcare environment that allows documentation sections to be efficiently repeated so that a healthcare provider can easily document medical data associated with care provided to a patient. Such duplicated documentation sections would also enable an enhanced analysis of the medical data provided within multiple documentation sections. Further, descriptive labels for each documentation section can provide valuable information that is easily accessible to healthcare providers.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Utilizing the methods and systems described herein, computerized systems, methods, computer storage media having computer-executable instructions embodied thereon for performing the disclosed methods, and user interfaces for generating medical documentation sets and for managing medical documentation sets are provided. In one aspect, the present invention provides one or more computer storage media having computer-executable instructions embodied thereon for performing a method for generating medical templates. In embodiments, an indication to generate a medical template is received. Medical categories, medical label elements, and medical documentation elements are obtained. Subsequently, a medical template is formatted using the obtained medical categories, label elements and documentation elements.

In another aspect, the present invention provides one or more computer storage media having computer-executable instructions embodied thereon for performing a method for generating medical documentation sets. In embodiments, an indication to generate a medical documentation set for a medical category is received. In response, a medical documentation set is presented within the medical category. The medical documentation set might include a replication of a medical template associated with the medical category, wherein the medical template includes medical label elements and medical documentation elements. The medical documentation set is captured

BRIEF DESCRIPTION OF THE SEVERAL VIEWS OF THE DRAWINGS

The present invention is described in detail below with reference to the attached drawing figures, wherein:

FIG. 6 is an illustrative screen display of an exemplary user interface for viewing a generated medical documentation set;

FIG. 7 is an illustrative screen display, in accordance with an embodiment of the present invention, of an exemplary user interface for viewing a documentation set labeling portion;

Figure 8:
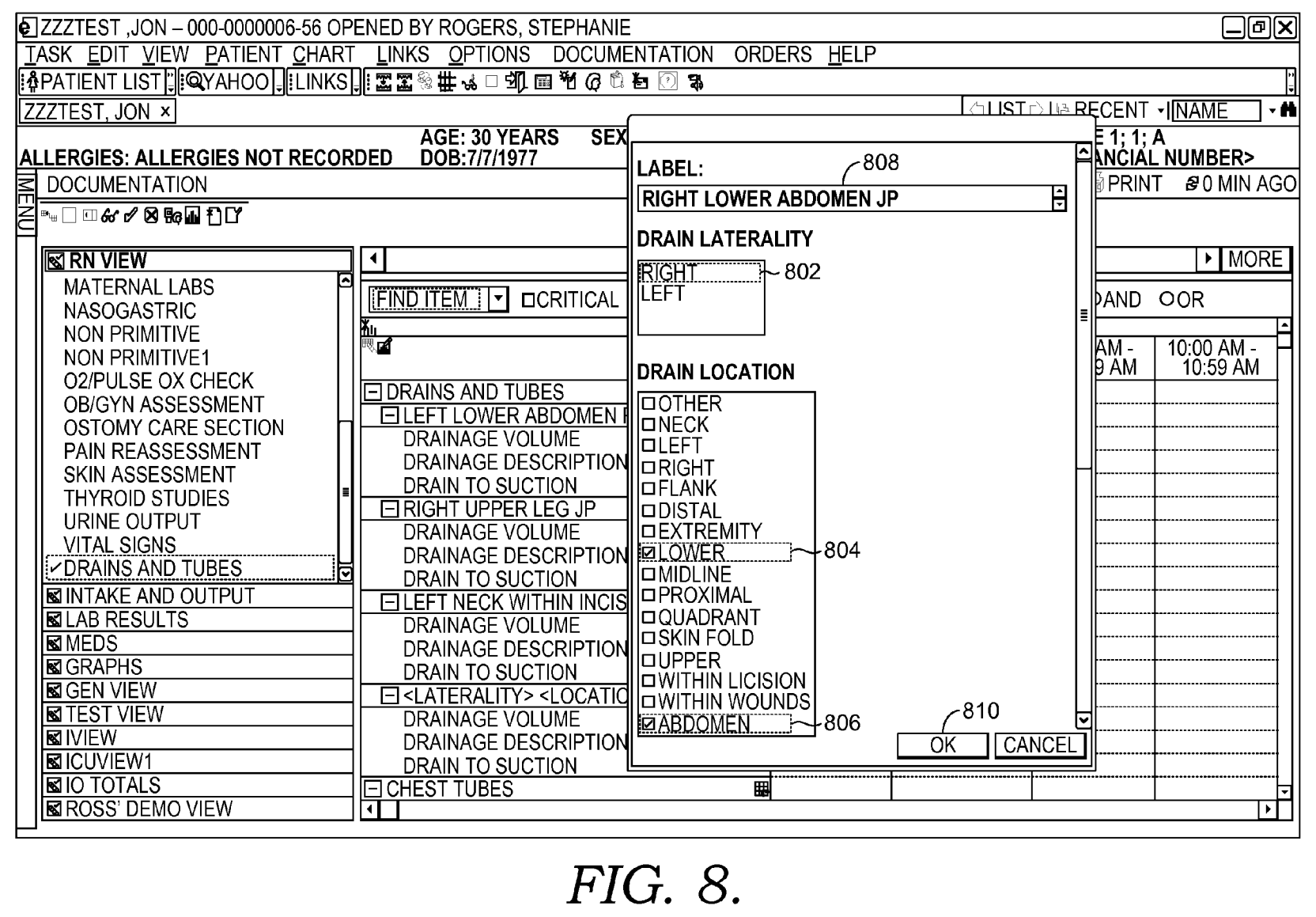

FIG. 8 is an illustrative screen display of an exemplary user interface for viewing a documentation set labeling portion having input in a plurality of medical label fields, in accordance with an embodiment of the present invention;

FIG. 9 is an illustrative screen display of an exemplary user interface for viewing a documentation set having a unique medical label, in accordance with an embodiment of the present invention;

Figure 10:
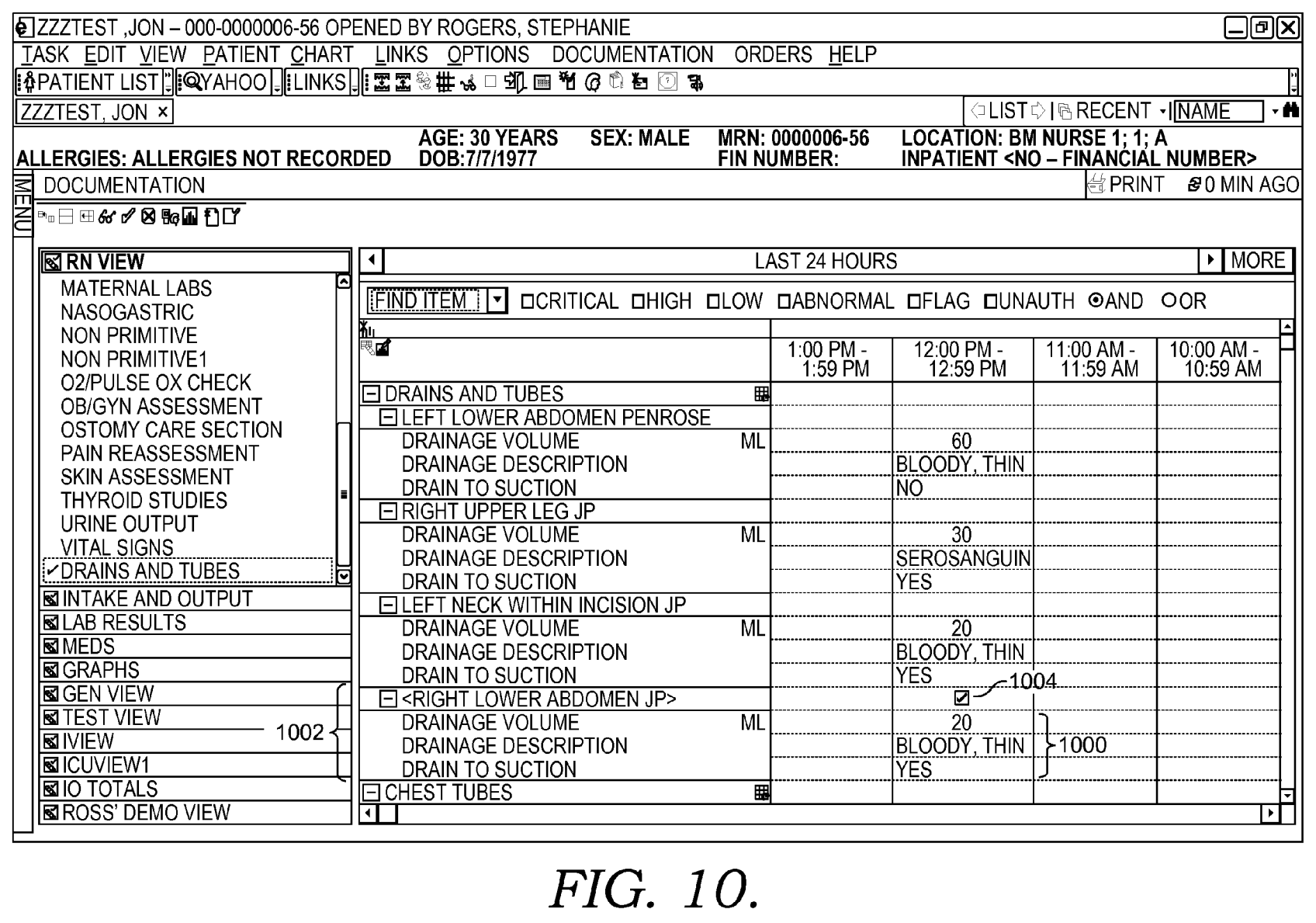

FIG. 10 is an illustrative screen display of an exemplary user interface for viewing a documentation set having medical data;

Figure 11:
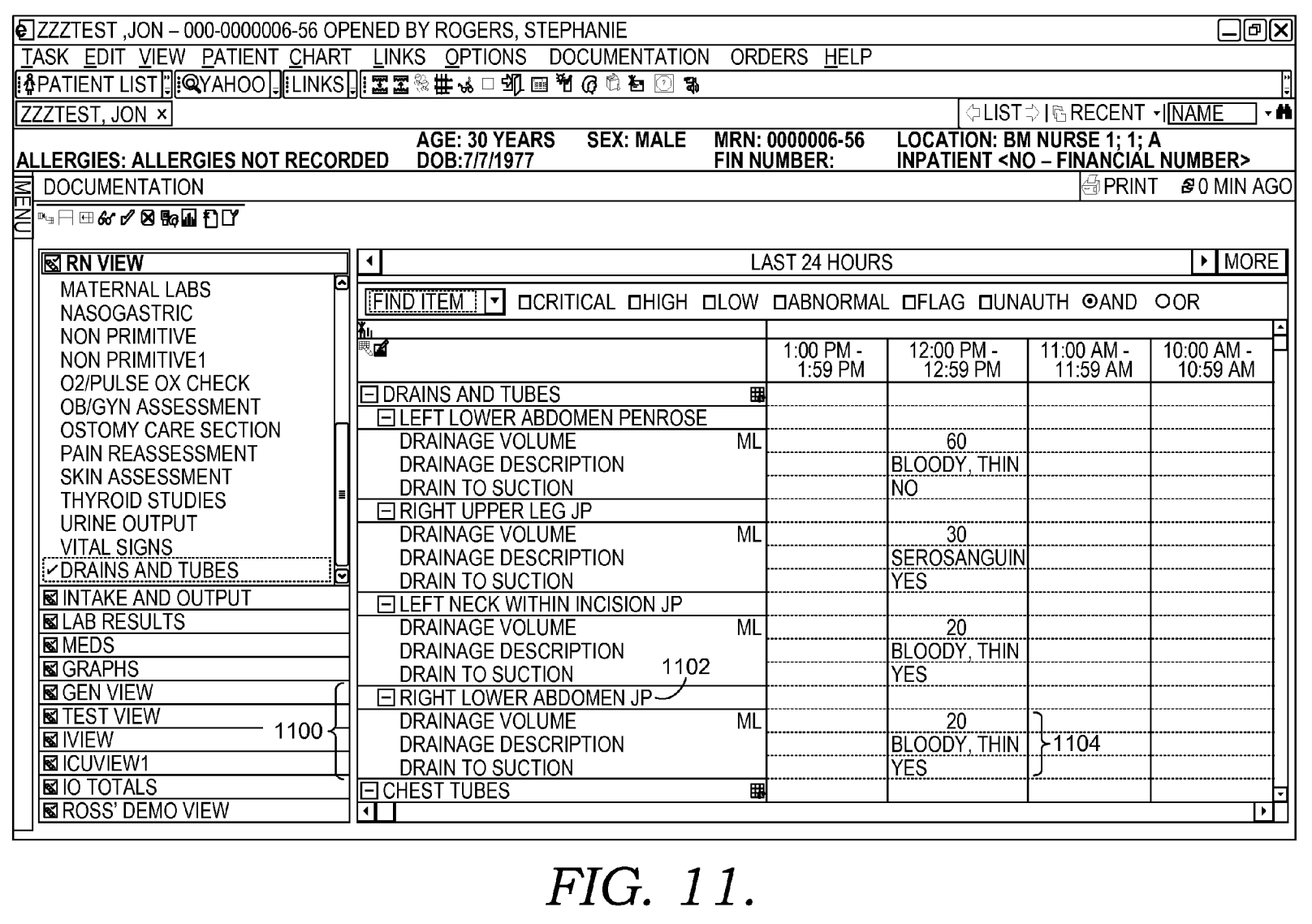

FIG. 11 is an illustrative screen display of an exemplary user interface for viewing a completed documentation set;

FIG. 12 is an illustrative screen display of an exemplary user interface for viewing medical documentation sets, in accordance with an embodiment of the present invention;

FIG. 13 is an illustrative screen display of an exemplary user interface for viewing a generated medical documentation set;

FIG. 14 is an illustrative screen display, in accordance with an embodiment of the present invention, of an exemplary user interface for viewing a documentation set labeling portion;

Figure 15:
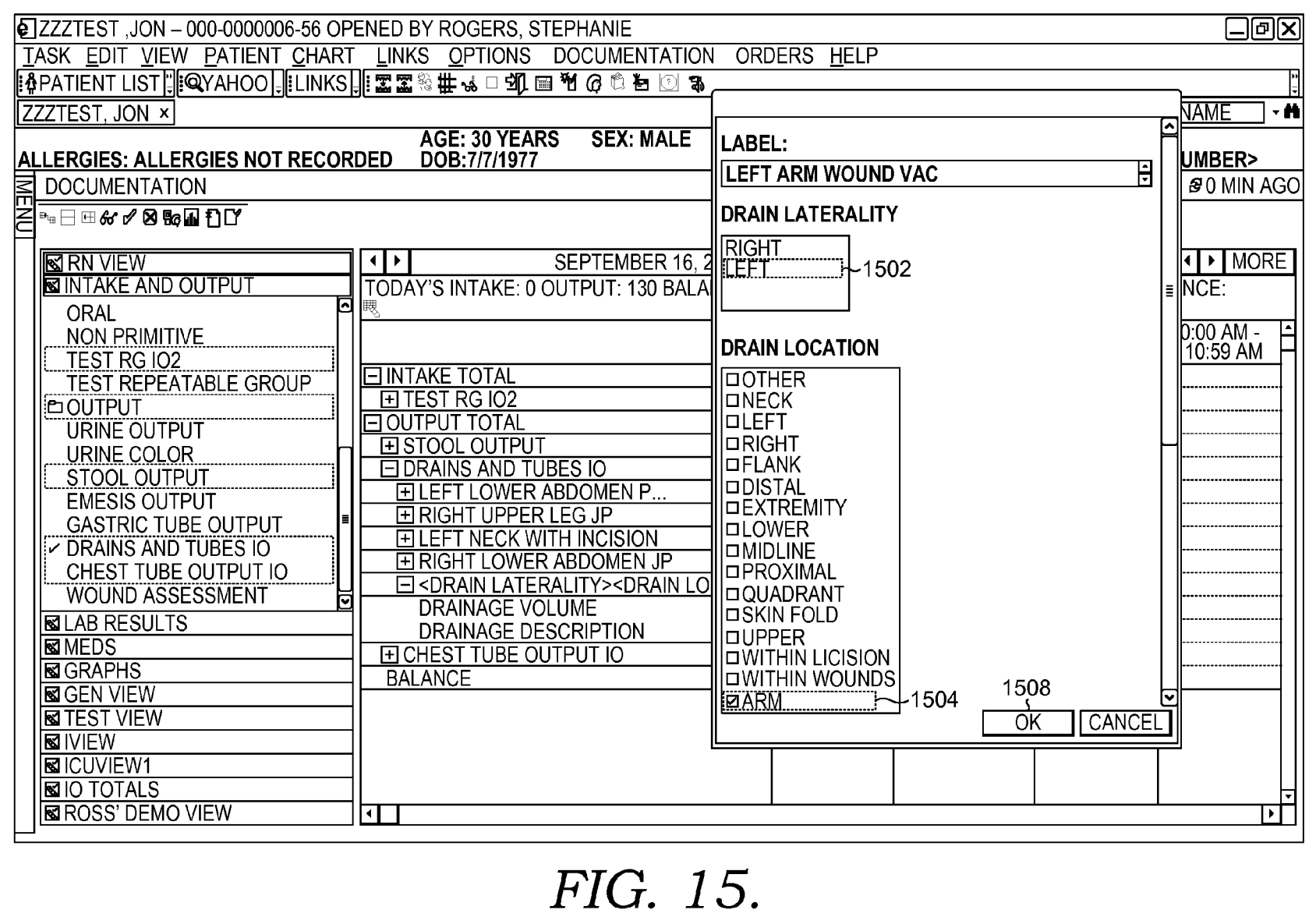

FIG. 15 is an illustrative screen display of an exemplary user interface for viewing a documentation set labeling portion having input in a plurality of medical label fields, in accordance with an embodiment of the present invention;

FIG. 16 is an illustrative screen display of an exemplary user interface for viewing a documentation set having a unique medical label, in accordance with an embodiment of the present invention;

FIG. 17 is an illustrative screen display of an exemplary user interface for viewing a documentation set having medical data;

FIG. 18 is an illustrative screen display of an exemplary user interface for viewing a completed documentation set; and FIG. 19 is an illustrative screen display, in accordance with an embodiment of the present invention, of an exemplary user interface for viewing the documentation set in a different documentation view.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention provide computerized methods and systems for generating and managing medical documentation. Utilizing the methods and systems described herein, a medical template is generated by obtaining medical categories, medical label elements, and medical documentation elements. A medical documentation set can be generated for a specific medical category using such a medical template. Upon receiving an indication to present a medical documentation set, the medical template is duplicated and/or presented so that medical data can be input into the medical documentation set. If desired, a unique medical label may be added to the medical documentation set. The medical documentation set can be captured so that it may be accessed and managed as desired.

Having briefly described embodiments of the present invention, an exemplary operating environment suitable for use in implementing embodiments of the present invention is described below.

Figure 1:
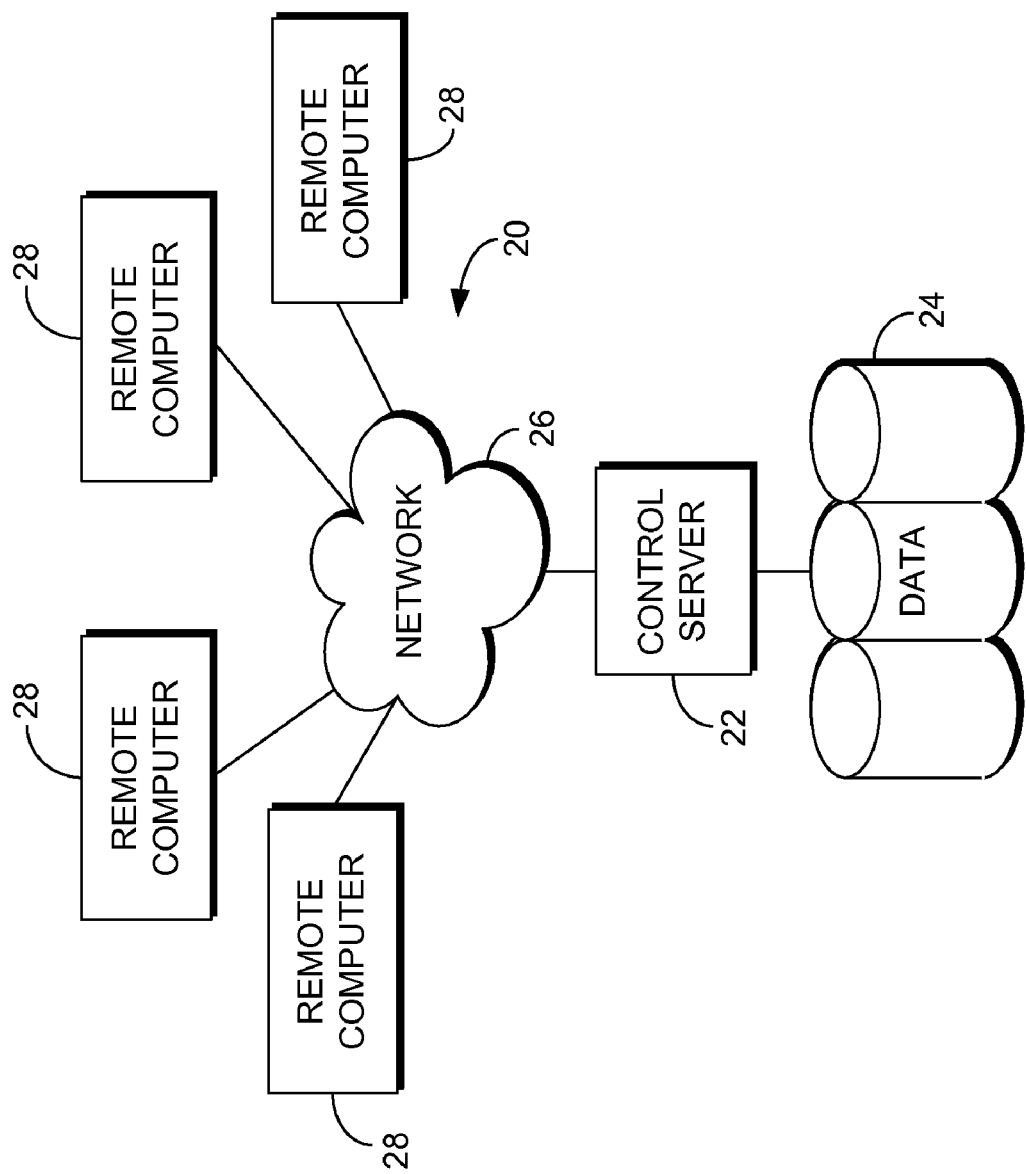
FIG. 1 is a block diagram of an exemplary computing environment suitable for use in implementing embodiments of the present invention.

Referring to the drawings in general, and initially to FIG. 1 in particular, an exemplary computing system environment, for instance, a medical information computing system environment, with which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in association with local and/or remote computer storage media including, by way of example only, memory storage devices.

With continued reference to FIG. 1, the exemplary medical information computing system environment 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer-readable media, for instance, database cluster 24. Computer-readable media can be any available media that may be accessed by server 22, and includes volatile and nonvolatile media, as well as removable and non-removable media. By way of example, and not limitation, computer-readable media may include computer storage media and communication media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 22. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 24, provide storage of computer-readable instructions, data structures, program modules, and other data for the control server 22.

The control server 22 may operate in a computer network 26 using logical connections to one or more remote computers 28. Remote computers 28 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the elements described above in relation to the control server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the control server 22 may include a modem or other means for establishing communications over the WAN, such as the Internet. In a networked environment, program modules or portions thereof may be stored in association with the control server 22, the database cluster 24, or any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., control server 22 and remote computers 28) may be utilized.

In operation, a clinician may enter commands and information into the control server 22 or convey the commands and information to the control server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 22. In addition to a monitor, the control server 22 and/or remote computers 28 may include other peripheral output devices, such as speakers and a printer.

Although many other internal components of the control server 22 and the remote computers 28 are not shown, those of ordinary skill in the art will appreciate that such components and their interconnection are well known. Accordingly, additional details concerning the internal construction of the control server 22 and the remote computers 28 are not further disclosed herein.

Although methods and systems of embodiments of the present invention are described as being implemented in a WINDOWS operating system, operating in conjunction with an Internet-based system, one of ordinary skill in the art will recognize that the described methods and systems can be implemented in any system supporting the receipt and processing of healthcare-related orders, particularly, sets of orders that define medication tapers. As contemplated by the language above, the methods and systems of embodiments of the present invention may also be implemented on a stand-alone desktop, personal computer, or any other computing device used in a healthcare environment or any of a number of other locations.

As previously mentioned, embodiments of the present invention relate to methods, systems, and computer-readable media for use in, e.g., a healthcare environment, for generating and/or managing one or more sets of medical documentation. For simplicity, the particular user will often be referred to herein as a clinician. However, it will be understood that the particular user may be any healthcare professional, physician, or other provider, as described above.

As used herein, the phrase "medical documentation set" refers to a set or group of associated medical documentation that is presented in an electronic form and may be used to document medical data. In one embodiment, a medical documentation set may include, among other things, fields for a medical label, medical label elements, medical documentation elements, medical data, or a combination thereof. A medical label, as used herein, identifies or designates a medical documentation set. In some cases, a global medical label is provided. A global medical label includes one or more medical label elements that indicate desired components of a medical label, e.g., location, type, date, event, etc. That is, a medical label element indicates a category (e.g., drain location) of label terms (e.g., neck, right, lower, proximal, quadrant, etc.) that can be selected to use to generate a unique medical label for association with a specific medical documentation set. In other cases, a unique medical label is provided to uniquely or descriptively identify a medical documentation set. As indicated, a unique medical label includes one or more label terms. In embodiments, the label terms medically describe care associated with a patient. For example, a medical label may describe aspects of a drain and, accordingly, may comprise "Left Lower Abdomen Penrose."

One skilled in the art will appreciate that a medical label of a medical template and/or a medical label of an initially presented medical documentation set might include a medical label having medical label elements. Thereafter, the medical label elements might be replaced with descriptive label terms such that a unique medical label results to specify the medical documentation set. In embodiments, a user selects the label terms to replace the medical label elements.

A medical documentation element, as used herein, identifies a medical aspect for which corresponding medical data may be documented. For example, a medical documentation element comprising "drainage volume" indicates that medical data providing an indication of drainage volume may be documented. In some embodiments, a medical documentation element may be positioned adjacent to or near one or more medical data fields that allow for documenting medical data. Medical data refers to any data associated with a medical documentation element that is documented in a medical data field within a medical documentation set. For example, assume a medical documentation element comprising "drainage volume" is presented within a medical documentation set. Medical data may include any data that indicates the drainage volume, such as, for example, 60 mL. Medical data might be documented by a clinician at the time of service or care.

One skilled in the art will appreciate that a medical documentation set can be generated based on a medical template. A medical template, as used herein, refers to a set of elements that define a unique format intended to be replicated for documenting medical data. A medical template may include one or more medical label elements that are used to define a medical label, medical documentation elements that identify medical data, and/or medical data fields that may, upon replication, receive medical data input within a medical documentation set. Upon the generation of a medical template, the medical template can be replicated, or otherwise used, to generate a medical documentation set having a form similar to the medical template such that a clinician can document medical data.

Figure 2:
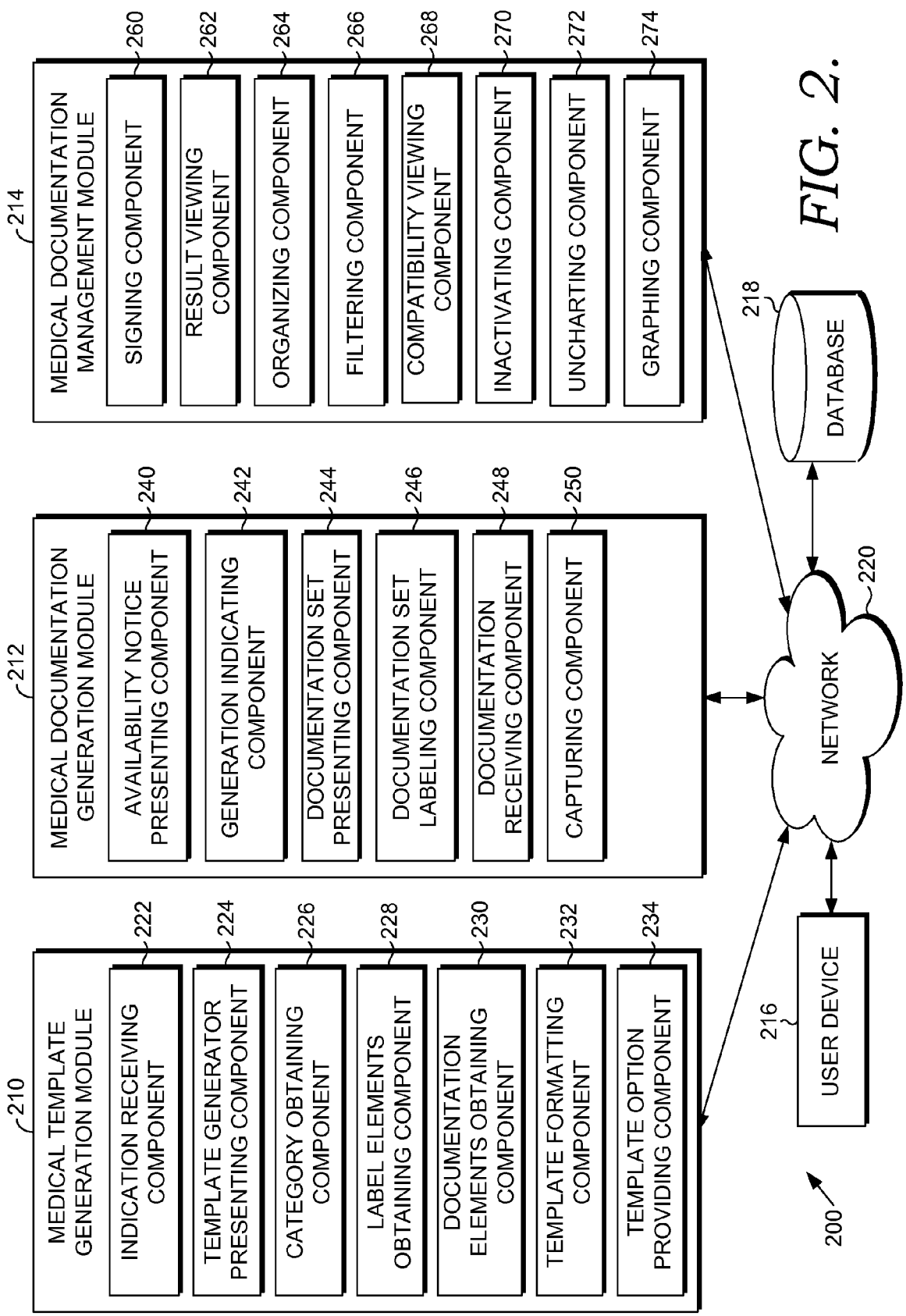
FIG. 2 is a block diagram of an exemplary computing system suitable for use in implementing embodiments of the present invention.

With reference to FIG. 2, an exemplary system suitable for use in implementing embodiments of the present invention is shown and designated generally as reference numeral 200. System 200 includes a medical template generation module 210, a medical documentation generation module 212, a medical documentation management module 214, a user device 216, and a database 218, all in communication with one another through a network 220. The network 220 may include, without limitation, one or more local area networks (LANs) and/or wide area networks (WANs). Such networking environments are commonplace in offices, enterprise-wide computer networks, intranets, and the Internet. Accordingly, the network 220 is not further described herein.

The database 218 is configured to store information associated with at least one medical category, medical template, or medical documentation set. In various embodiments, such information may include, without limitation, a medical category, a medical label, a medical label element, a medical documentation element, a medical datum, a combination thereof, or the like. Medical categories might be based on patients, medications, medical conditions, medical symptoms, medical procedures, medical assessments, or any other aspect for which data documentation may be categorized. For example, medical categories may include drains and tubes, IV sites, patient education, skin assessment, pain assessment, and the like. Such medical categories enable organization and management of medical templates, medical documentation sets, and the like.

In embodiments, the database 218 is configured to be searchable for one or more patients, medical categories, medical label, medical label elements, medical documentation elements, medical data, and/or associated values stored in association therewith. It will be understood and appreciated by those of ordinary skill in the art that the information stored in the database 218 may be configurable and may include any information relevant to a medical category, a medical label, a medical label element, a medical documentation element, a medical datum, and/or a case or patient associated therewith. The content and volume of such information are not intended to limit the scope of embodiments of the present invention in any way. Further, though illustrated as a single, independent component, database 218 may, in fact, be a plurality of databases, for instance, a database cluster, portions of which may reside on a computing device associated with the medical template generation module 210, the medical documentation generation module 212, the medical documentation management module 214, the user device 216, another external computing device (not shown) and/or any combination thereof.

The medical template generation module 210 includes various components and is configured to generate a medical template. Such a medical template may be used to generate one or more medical documentation sets. Clinicians, program developers, program managers, and the like, may utilize medical template generation module 210 to generate a medical template. In such a case, a clinician, program developer, program manager, or the like may generate a medical template upon determining that a medical template may be beneficial for a specific medical category or upon determining that a medical template modification may be beneficial. For example, assume a medical category comprises "drains and tubes." Upon determining that an abundant amount of time is spent creating medical documentation sets for "drains and tubes," a clinician may generate a medical template for use in generating future medical documentation sets to reduce the amount of time spent on generating future medical documentation sets for the "drains and tubes" medical category. Alternatively, a clinician, program developer, program manager, or the like may generate a medical template at the outset such that medical templates are prepared and ready for use by a clinician.

One skilled in the art will recognize that medical template generation module 210 may be used to generate any number of medical templates. In one embodiment, one general medical template may be generated that may be globally used. That is, regardless of the medical category, the global medical template may be a basis for generating a medical documentation set. In another embodiment, a medical template may be generated for each medical category deemed appropriate. For example, assuming a clinician or system administrator deems medical templates beneficial for drains and tubes, IV sites, patient education, skin assessment, and pain assessment, different medical templates may be generated for each of such medical categories.

The medical template generation module 210 may include an indication receiving component 222, a template generator presenting component 224, a category obtaining component 226, a label elements obtaining component 228, a documentation elements obtaining component 230, a template formatting component 232, and a template option providing component 234. One skilled in the art will recognize that any number of components may be utilized to generate a medical template.

The indication receiving component 222 is configured to receive an indication to generate a medical template. In one embodiment, indication receiving component 222 may receive an indication to generate a medical template upon a clinician indicating such a desire. For example, a clinician or program developer may select a selectable medical template generator tool, represented by an icon, folder, file, or link, to indicate a desire to generate a medical template. Alternatively, indication receiving component 222 may automatically receive an indication to generate a medical template in association with each instance, for example, that medical information computer system 20 of FIG. 1 is accessed, a software application is accessed, a patient is selected, a documentation view is selected, or a medical category is selected. In such a case, in one implementation, indication receiving component 222 might only automatically receive an indication to generate a medical template in an instance where a medical template does not exist or a limited number of medical templates exist in association with a particular medical information computer system, software application, patient, documentation view, medical category, or the like. The terms "individual," "person," and "patient" are used interchangeably herein and are not meant to limit the nature of the referenced individual in any way. Rather, the methods and systems described herein are equally applicable, for instance, in a veterinary setting. Further, use herein of the term "patient" is not meant to imply any particular relationship between the individual in question and those generating medical templates, generating medical documentation sets, managing medical documentation sets, and the like. A software application may include, for example, PowerChart®, Power Chart Office®, and other Cerner Millennium® applications marketed by the Cerner Corporation of Kansas City, Mo. A documentation view refers to a view having specific information within a software application, such as, for example, Interactive View, Intake and Output View, or RN View within the PowerChart® application marketed by Cerner Corporation.

The template generator presenting component 224 is configured to present a medical template generator tool for use by a clinician, program developer, program administrator, or the like. Such a medical template generator tool may be used to generate a medical template. One skilled in the art will recognize that a medical template generator tool can take any form. In one embodiment, the template generator presenting component 224 might present a medical template generating dialogue to allow a clinician or program developer to specify aspects of the medical template, such as one or more medical categories, medical label elements, and medical documentation elements.

The category obtaining component 226 is configured to obtain one or more medical categories. An obtained medical category may be used to associate the medical template with a medical category so that the medical template may be used appropriately. Accordingly, the medical template may be associated with a specific patient, medical condition, medical procedure, medical assessment, or the like. Category obtaining component 226 may obtain one or more medical categories by identifying, receiving, retrieving, or determining such a medical category. A template generator presenting component 224 may be utilized to obtain a medical category. In one embodiment, category obtaining component 226 obtains a medical category upon a clinician or program developer indicating a medical category. For example, a clinician or program developer may indicate a medical category by selecting a medical category from a list, e.g., a drop down menu or a search results list, inputting a medical category, or the like.

The label elements obtaining component 228 is configured to obtain one or more medical label elements. Label elements obtaining component 228 may obtain one or more label elements by identifying, receiving, retrieving, or determining such label elements. A template generator presenting component 224 can be utilized to obtain one or more label elements. In one embodiment, label elements obtaining component 228 obtains label elements upon a clinician or program developer indicating one or more medical label elements. For example, a clinician or program developer may indicate a label element by selecting the label element from a list, e.g., a drop down menu or search results list, inputting a label element, or the like. Where a clinician or program developer indicates a label element by selecting the label element from a list, the list of potential label elements might be based on the medical category obtained by category obtaining component 226. For example, assume category obtaining component 226 obtains a "drains and tubes" medical category. In such a case, potential label elements provided within a list may include, for example, drain number, drain section control, drain status, drain tube comment, drain number, drainage, drainage amount, drainage characteristics, drainage color, drainage description, drain laterality, drain location, drain type, and the like.

The documentation elements obtaining component 230 is configured to obtain medical documentation elements. Documentation elements obtaining component 230 may obtain one or more medical documentation elements by identifying, receiving, retrieving, or determining such medical documentation elements. A template generator presenting component 224 may be utilized to obtain one or more documentation elements. In one embodiment, documentation elements obtaining component 230 obtains medical documentation elements upon a clinician or program developer indicating one or more medical documentation elements. For example, a clinician or program developer may indicate a medical documentation element by selecting the medical documentation element from a list, e.g., a drop down menu or search results list, inputting a medical documentation element, or the like. Where a clinician or program developer indicates a medical documentation element by selecting the medical documentation element from a list, the list of potential medical documentation elements can be based on the medical category obtained by category obtaining component 226 and/or the medical label elements obtained by label elements obtaining component 228. For example, assume category obtaining component 226 obtains a "drains and tubes" medical category. In such a case, potential medical documentation elements provided may include, for example, drain dressing type, drainage description, drain insertion date/time, drain inserted by, drainage volume, drain to suction, and the like.

The template formatting component 232 is configured to format the medical template. In one embodiment, the template formatting component 232 aggregates the medical label elements obtained by label elements obtaining component 228 and the medical documentation elements obtained by documentation elements obtaining component 230. In addition, the template formatting component 232 might be configured to determine an arrangement of elements and medical data fields.

The template option providing component 234 is configured to provide options for the medical template. In one embodiment, the template option providing component 234 provides an option to capture or save the medical template such that the medical template may be accessed, retrieved, or utilized at a later time. The template option providing component 234 might capture the medical template automatically or upon receiving an indication to capture the medical template, e.g., a clinician selects a "Save" or "Submit" button. In such a case, template option providing component 234 can associate a medical template name with the medical template. Such a medical template name may be a default name based on, for example, the medical category, medical label elements, medical documentation elements, or the like.

Alternatively, the template option providing component 234 may present a capturing dialogue to allow a clinician or program developer to specify the name of the medical template, the folder location for saving the medical template, or a combination thereof. In the embodiment where a capturing dialogue is presented, a default medical template name and/or default folder location might be specified. For example, the default name may be the medical category for which the medical template is to be used followed by the word "Template." In such an embodiment, although a default medical template name and/or default folder location may be specified, the clinician or program developer may be permitted to modify the medical template name or the default folder location. One skilled in the art will recognize that a medical template name may be associated with the medical template at any time during medical template generation.

In one embodiment, the template option providing component 234 provides an option to verify the medical template. In such an embodiment, if a clinician or program developer selects to verify the medical template, the formatted medical template is presented to the user. Accordingly, a clinician or program developer can verify that label elements and/or documentation elements correspond with the appropriate medical category. The template option providing component 234 may also provide a clinician or program developer an option to modify the medical template. Such modifications may include adding a label element or a documentation element, removing a label element or a documentation element, modifying the format of the template, e.g., changing position of elements, and the like.

The medical documentation generation module 212 includes various components and is configured to generate one or more medical documentation sets. In some embodiments, the medical template generated by the medical template generation module 210 is utilized by the medical documentation generation module 212 to generate one or more medical document sets. In other embodiments, any medical template may be utilized by the medical documentation generation module 212 to generate one or more medical documentation sets. The medical documentation generation module 212 may include an availability notice presenting component 240, a generation indicating component 242, a documentation set presenting component 244, a documentation set labeling component 246, a documentation receiving component 248, and a capturing component 250.

The availability notice presenting component 240 is configured to present a medical template availability notice in instances where a medical template is deemed available. A medical template availability notice indicates that a medical template may be used to generate a medical documentation set, if the clinician so desires. For example, a medical template availability notice might be deemed available if a medical template associated with a specific medical category exists. In an alternative embodiment, a medical template might always be deemed available and, thus, a medical template availability notice may be presented.

A medical template availability notice presented to a clinician may include, for example, an icon, a sound, text, a value, a selectable "add a medical documentation set" button, or a unique formatting thereof. Further, the medical template availability notice can be selectable such that a clinician can select the medical template availability notice to initiate the generation of a medication documentation set. In an embodiment where medical templates are associated with a particular medical category, the medical template availability notice may be positioned near or adjacent to the medical category with which it is associated. Accordingly, where multiple medical categories are presented, multiple medical template availability notices may also be presented. In embodiments where a general medical template exist, the medical template availability notice may be positioned at a specific location within the user interface.

The generation indicating component 242 is configured to receive an indication to generate a medical documentation set. In one embodiment, generation indicating component 242 receives an indication to generate a medical documentation set upon a clinician indicating such a desire. For example, a clinician might select a generation indicator, such as an icon, folder, file, or link, to indicate a desire to generate a medical documentation set. Alternatively, generation indicating component 242 automatically receives an indication to generate a medical documentation set in association with each instance, for example, that medical information computer system 20 of FIG. 1 is accessed, a software program is accessed, a patient is selected, a documentation view is selected, a medical category is selected, or the like.

Documentation set presenting component 244 is configured to present a medical documentation set in the form of the appropriate medical template, such as a medical template generated by medical template generation module 210. As used herein, form refers to format, content, programming code, or a combination thereof. In some embodiments, documentation set presenting component 244 duplicates or copies the appropriate medical template to present a medical documentation set in the form of the appropriate medical template. In other embodiments, documentation set presenting component 244 generates the medical documentation set in accordance with the form of an appropriate medical template to present the medical documentation set.

In some cases, only one medical template is available. In such a case, documentation set presenting component 244 presents a medical document set based on the form of the only available medical template. In alternative cases, multiple medical templates are available. As such, documentation set presenting component 244 presents a medical documentation set based on the form of a default medical template or based on the form of a medical template associated with a specific medical category. For example, assume each medical category within an application includes an associated medical template. Further assume that a clinician indicates a desire to generate a medical documentation set by selecting an icon near or adjacent to the "drains and tubes" medical category. As a result, documentation set presenting component 244 might present a medical documentation set according to the form of the medical template associated with the "drains and tubes" medical category.

In some cases, although a medical template having multiple medical documentation elements may be associated with a specific medical category, not all documentation elements may be desired to be presented within a medical documentation set. For example, in a first documentation view, a clinician might desire to have all medical documentation elements presented within the medical documentation set. In a second documentation view, however, the clinician might prefer to have only a select few medical documentation elements presented within the medical document set, e.g., to increase efficiency or maximize relevant data displayed on a display monitor. In such cases, documentation set presenting component 244 can also be configured to determine the medical documentation elements to present within the medical documentation set. Accordingly, documentation set presenting component 244 might determine the specific documentation view and which of the medical documentation elements to present within the medical documentation set.

Documentation set presenting component 244 might present the medical documentation set in a specific default location. Such default locations may include, for example, the bottom or end of medical documentation sets for a particular medical category, the beginning or top of medical documentation sets for a particular medical category, the location of a highlighted portion or selected portion, or an appropriate alphabetic or numeric location, e.g., alphabetize by medical label. In other embodiments, documentation set presenting component 244 receives an indication from a user specifying the location of the desired medical documentation set.

The documentation set labeling component 246 is configured to provide a unique medical label for a documentation set. Such a unique medical label can replace the label elements included in the initial medical documentation set. In one embodiment, documentation set labeling component 246 is configured to receive an indication that a unique label is desired. In some embodiments, such an indication can be generated based on a clinician indication. A clinician may indicate such a desire, for example, by selecting to provide a unique label. Such a selection may occur, for example, in instances where a clinician selects, or clicks, on the medical label or medical label elements initially presented with the medical documentation set.

Documentation set labeling component 246 may be configured to present label terms useable for a unique medical label such that a clinician can select descriptive terms for the medical label. In some embodiments, documentation set labeling component 246 automatically presents label terms. For example, upon adding a medical documentation set to an application, documentation view, or medical category, label terms are automatically presented to a clinician. In an alternative embodiment, label terms are presented to a clinician upon receiving an indication that a unique label is desired.

Label terms presented by documentation set labeling component 246 might be associated with a specific medical category or label elements. For example, assume medical template generation module 210 formats a medical template associated with the medical category "drains and tubes" as having label elements "drain laterality," "drain location," and "drain type." In such a case, documentation set labeling component 246 can present label terms associated with "drain laterality," "drain location," and "drain type," such that a clinician may select appropriate descriptive terms.

Documentation set labeling component 246 may also be configured to receive an indication of label terms desired for the medical label. An indication of such a desired medical label can be provided by a clinician. A clinician may provide an indication of a desired medical label by selecting label terms presented to the clinician. For example, assume a clinician is presented with multiple terms for each label element, e.g., drain laterality, drain location, and drain type. The clinician may select one of the terms for each label element to provide an indication of label terms desired for the medical label. Such a selection may be performed for each label element in sequential dialogue boxes or within the same dialogue box. The documentation set labeling component 246 can also be configured to present the unique label within the medical documentation set such that the medical documentation set is easily identified.

The documentation receiving component 248 is configured to receive medical data. Such medical data may be entered or selected by a clinician as a result of operating, examining, or assessing a patient. In one embodiment, a clinician initiates medical data documentation at the medical data field, the associated documentation element, the associated medical label, the associated medical category, or the like. A clinician may select the medical data fields to use for entering medical data. Alternatively, a clinician may be required to provide medical data for each medical data field. In such a case, the clinician may provide default medical data, e.g. Not Applicable, in instances where such medical data does not exist.

The documentation receiving component 248, in some embodiments, may only be enabled to receive medical data in instances where a unique medical label has been provided. As such, where a medical documentation set has a medical label comprising medical label elements, the documentation receiving component 248 might prevent medical data from being entered into medical data fields.

In addition to receiving medical data, in one embodiment, documentation receiving component 248 provides a conditionality function. Such a conditionality function determines whether a predetermined attribute exists within a medical data field. A predetermined attribute may comprise, for example, specific text (e.g., bloody), a specific value or value range (e.g., 10 or 10-20), a symbol (e.g., +), or other data attribute. If a predetermined attribute exists within a medical data field, the documentation receiving component 248 may provide an opportunity for further documentation. Accordingly, the documentation receiving component 248 can provide additional medical data fields, medical documentation elements, medical documentation sets, and the like. The additional fields may be added automatically or upon receiving an indication to provide such fields. The additional documentation fields can be presented as an extension of the initial medical documentation set or, alternatively, presented as a new medical documentation set. Such a conditionality function allows a clinician the ability to quickly document medical data that would otherwise be undocumented or would require the clinician to generate a new medical template, medical documentation set, or medical data field.

By way of example only, assume the text "bloody" is identified as a predetermined attribute. Assume further that a clinician enters the text "bloody" in a medical data field that is associated with the medical documentation element "drainage description." The documentation receiving component 248 might determine that the predetermined attribute "bloody" exists within a medical data field. As such, the documentation receiving component 248 may provide another medical documentation element titled "blood amount" and one or more corresponding medical data fields within the initial medical documentation set.

The capturing component 250 is configured to capture or save the medical documentation set such that the medical documentation set may be accessed at a later time. The medical documentation set can be captured automatically, e.g., a specific time has elapsed or a clinician selects a different documentation view, or upon receiving an indication to capture the medical documentation set, e.g., a clinician selects "Save" or "Submit" button. The capturing component 250 might present a capturing dialogue to allow a clinician to specify the name of the medical documentation set, the medical category, or the patient associated with the medical category, the folder location for saving the medical documentation set, or a combination thereof. In the embodiment where a capturing dialogue is presented, a default name and/or default folder location may be specified. In such an embodiment, although a default name and/or default folder location may be specified, the clinician may be permitted to modify the name or the default folder location.

One skilled in the art will recognize that capturing component 250 may capture the medical documentation set at any time during generation or management of the medical document set. For example, upon documentation set presenting component 244 presenting a documentation set in the form of the appropriate medical template, capturing component 250 might capture the medical documentation set even though a unique label and medical data has yet to be associated with the medical documentation set. Accordingly, a clinician may prepare medical documentation sets for a particular medical category in advance of inputting medical data.

The medical documentation management module 214 includes various components and is configured to manage one or more medical documentation sets. The medical documentation management module 214 includes a signing component 260, a result viewing component 262, an organizing component 264, a searching component 266, a compatibility viewing component 268, an inactivating component 270, an uncharting component 272, and a graphing component 274.

The signing component 260 is configured to receive an indication to sign the medical label and/or medical data within a medication documentation set. In one embodiment, such an indication may be provided by a clinician. A clinician may provide an indication to sign the medical label and/or medical data, for example, by selecting a selectable box, icon, link, or the like. Upon receiving an indication to sign the medical label and medical data, signing component 260 may be configured to fix the medical label, e.g., remove brackets surrounding the medical label or other indicator, as well as the medical data.

The result viewing component 262 is configured to present result details for a specific medical data result within a medical documentation set and/or results associated with a specific medical label. The result viewing component 262 might present result details upon receiving an indication, for example, from a clinician, that viewing result details is desired. A clinician may provide such an indication by selecting a specific medical data result or a specific medical label and, thereafter, selecting a "view result details" link. By way of example, assume a clinician selects a medical data result within a medical documentation set, e.g., right clicks while the selector hovers over the medical data result, and, thereafter, selects a "view result details" link. In such a case, result viewing component 262 may present the result and, among other things, the associated medical label. Now assume a clinician selects a medical label within a medical documentation set, e.g., right clicks while the selector hovers over the medical label, and thereafter, selects a "view result details" link. In such a case, result viewing component 262 may present medical label details, e.g., label history including valid dates, creator, status, and the like.

The organizing component 264 is configured to organize medical documentation sets such that medical documentation sets may be, for example, collapsed and expanded. In one embodiment, organizing component 264 may present an option to collapse, expand, close, remove, collapse all, and expand all. Upon receiving an indication to organize one or more medical documentation sets, the organizing component 264 may organize the medical documentation sets accordingly. Where the "collapse" option is selected, the medical documentation set specified may collapse such that only the medical label is displayed. Alternatively, to collapse a specific medical documentation set, a clinician may select an icon, e.g., a negative sign, located adjacent to the medical label. Where the "collapse all" option is selected, for example, by a clinician, all medical documentation sets within a medical category may collapse such that only the medical label is displayed. Where the "expand" option is selected, the contents of the entire medical documentation set specified is displayed. Alternatively, to expand a specific medical documentation set, a clinician may select an icon, e.g., a plus sign, located adjacent to the medical label. Where the "expand all" option is selected, for example, by a clinician, all medical documentation sets within a specific medical category may be displayed.

The searching component 266 is configured to search for and display medical data results associated with a particular documentation element. The searching component 266 might be configured to present a search box such that a clinician can enter or select a medical documentation element for which search results are desired. Upon receiving a search term, searching component 266 can present search results associated with the entered or selected documentation element. For example, assume a clinician selected the documentation element "drainage volume." Upon receiving such a selection, searching component 266 searches for and presents medical data results that are associated with the drainage volume documentation element.

The compatibility viewing component 268 is configured to present medical documentation sets in a documentation view different than the documentation view in which the medical documentation set was generated. For example, assume a medical documentation set is generated in a first view, e.g., RN View. Further assume that after the medical documentation set was generated, a clinician utilizes a second view, e.g., Intake and Output View. In such a case, compatibility viewing component 268 can present within the Intake and Output View the medical documentation set generated within the RN View. In some embodiments, compatibility viewing component 268 is configured to determine the documentation elements to present within the view. For example, some views may necessitate or desire each of the documentation elements set forth in the medical template to be displayed, while other views may prefer only a portion of the documentation elements set forth in the medical template to be displayed.

In some embodiments, compatibility viewing component 208 automatically presents medical documentation sets in a different documentation view. As such, after a medical documentation set is generated within a first view, the medical documentation set, or modified version, is automatically presented within a second view. Such an automatic presentation can be performed immediately or upon a clinician's access of the additional view. In other embodiments, compatibility viewing component 268 presents medical documentation sets in a different documentation view upon receiving an indication, such as, for example, from a clinician, that compatibility viewing is desired.

The inactivating component 270 is configured to inactivate a medical documentation set. Inactivating component 270 might inactivate a medical documentation set automatically or upon a clinician indication. Such a clinician indication may include, for example, right clicking within the medical documentation set and selecting an "inactivate" link. Alternatively, a clinician may indicate a desire to inactive a medical documentation set by opening a customize dialog box and selecting the medical documentation set(s) desired to be inactivated. A clinician might desire to inactivate a medical documentation set when the medical documentation set is no longer in use, e.g., a drain or tube is removed from a patient.

An inactivated medical documentation set may be displayed with an indication, e.g., a grey background, that the particular medical documentation set is inactivated so as to provide notification of such an inactivation. In some embodiments, inactivating component 270 is configured to continue to display the medical data and documentation elements until a specific time or event or until a specific time has elapsed. For example, where no medical data exists for the time frame displayed, the inactive medical documentation set may be removed from the view automatically.

The uncharting component 272 is configured to unchart a medical label and/or documentation elements and associated medical data. The uncharting component 272 might unchart documentation elements and/or a medical label based on an indication to unchart such a label or element, e.g., a clinician selects to unchart. In one embodiment, to unchart a medical label, all the documentation elements may also be required to be uncharted. Where a medical label is uncharted, the medical documentation set may be automatically inactivated and, in some cases, may be displayed as "in error."

Uncharting component 272 may, in some embodiments, require a reason for uncharting a medical label and/or documentation elements. In such an embodiment, sufficient reasons might include charted on incorrect order, charted at incorrect time, charted on incorrect patient, and other. The uncharting component 272 may also enable a clinician to view result details for uncharted label. Such result details may include the medical label name and associated valid time period, the creator of the medical label, the status of the medical label, and the reason for the uncharted label.

The graphing component 274 is configured to present graphs based on documentation sets. In one embodiment, graphing component 274 graphs the medical data associated with a specific documentation element by medical label. For example, assume a clinician would like to compare different chest tube drainage areas for a patient. The graphing component 274 may graph, via a bar graph, line graph, pie chart, or the like, the medical data associated with chest tube drainage for each medical documentation set. In addition, graphing component 274 can present the medical labels associated with each documentation element so that the chest tube drainage may be easily compared.

As previously mentioned, the system 200 further includes a user device 216 in communication with the database 218, the medical template generation module 210, the medical documentation generation module 212, and the medical documentation management module 214 via the network 220. The user device 216 may be associated with any type of computing device, such as computing device 100 described with reference to FIG. 1, for example. Though not shown in FIG. 2, the user device 216 typically includes at least one presentation module configured to present (e.g. display) medical templates and/or medical documentation sets.

It will be understood and appreciated by those of ordinary skill in the art that other components not shown may also be included with the system 200. Further, additional components not shown may also be included within any of the database 218, the medical template generation module 210, the medical documentation generation module 212, the medical documentation management module 214, and the user device 216. Additionally, any components illustrated in FIG. 2 in association with the medical template generation module 210, the medical documentation generation module 212, or the medical documentation management module 214 may additionally or alternatively be associated with any of the other illustrated modules, the user device 216, and/or another external computing device, e.g., a server (not shown). Any and all such variations are contemplated to be within the scope of embodiments hereof.

Figure 3:
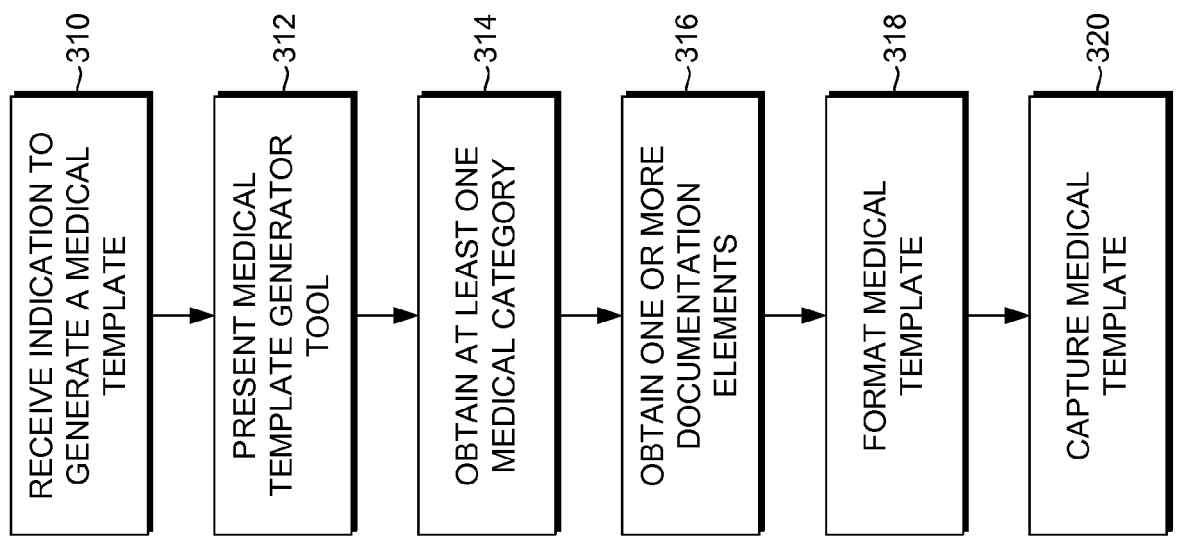
FIG. 3 is a flow diagram showing a method for generating a medical template, in accordance with an embodiment of the present invention.

Turning now to FIG. 3, a flow diagram showing a method for generating a medical template, in accordance with an embodiment of the present invention, is illustrated and designated generally as reference numeral 300. Method 300 may be implemented on the above-described exemplary computing system environment (FIG. 1) and, by way of example only, may be utilized by a clinician, program developer, or program administrator to generate a medical template.

Initially, as indicated at block 310, an indication to generate a medical template is received. At block 312, a medical template generator tool is presented. Thereafter, at block 314, at least one medical category is obtained. One or more label elements are obtained at block 316. Subsequently, at block 318, one or more documentation elements are obtained. Upon obtaining one or more documentation elements at block 318, a medical template is formatted. This is indicated at block 320. The medical template is captured at block 322.

Figure 4:
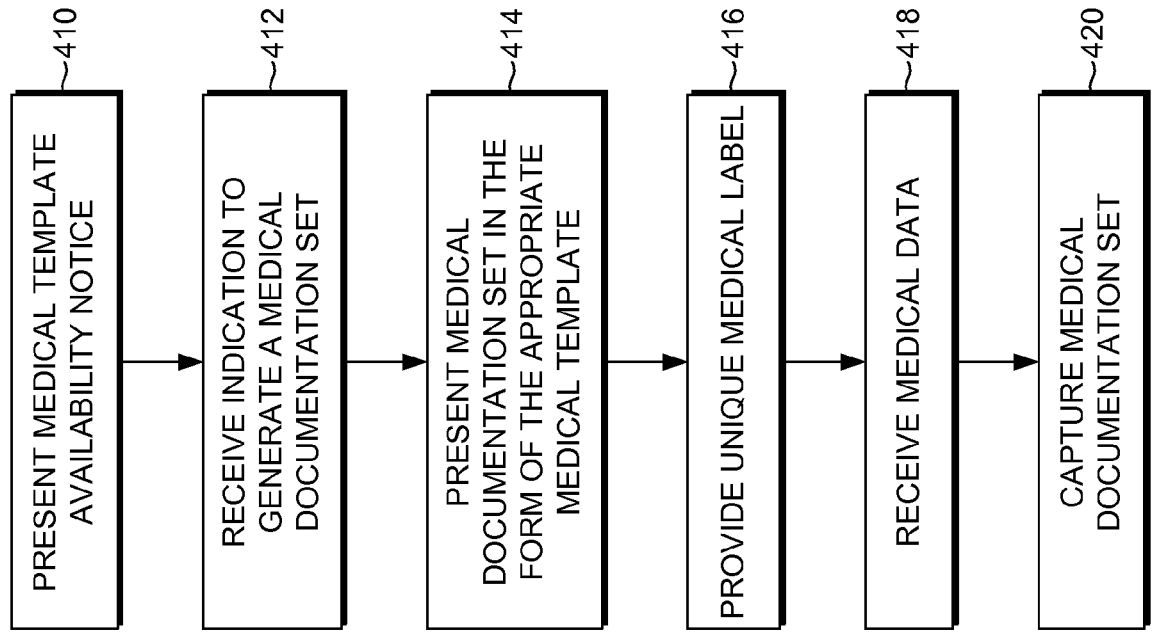
FIG. 4 is a flow diagram showing a method for generating a medical documentation set.

With reference to FIG. 4, a flow diagram showing a method for generating a medical documentation set, in accordance with an embodiment of the present invention, is illustrated and designated generally as reference numeral 400. Method 400 may be implemented on the above-described exemplary computing system environment (FIG. 1) and, by way of example only, may be utilized by a clinician, program developer, or program administrator to generate a medical template.

Initially, as indicated at block 410, a medical template availability notice is presented. Thereafter, an indication to generate a medical documentation set is received at block 412. At block 414, a medical documentation set in the form of the appropriate medical template is presented. A unique medical label is provided for the medical documentation set at block 416. Medical data is received at block 418. The medical documentation set is captured at block 420.

FIGS. 5-20 illustrate exemplary displays of graphical user interfaces for generating a medical documentation set, according to embodiments of the present invention. The graphical user interfaces may be any electronic display wherein clinicians have access to generate a medical documentation set. The graphical user interfaces described herein may be displayed on user device 216 of FIG. 2. A clinician can interact with the graphical user interfaces using well known input components—such as, for example, a mouse, joystick, stylus, touch screen, keyboard, or the like.

Figure 5:
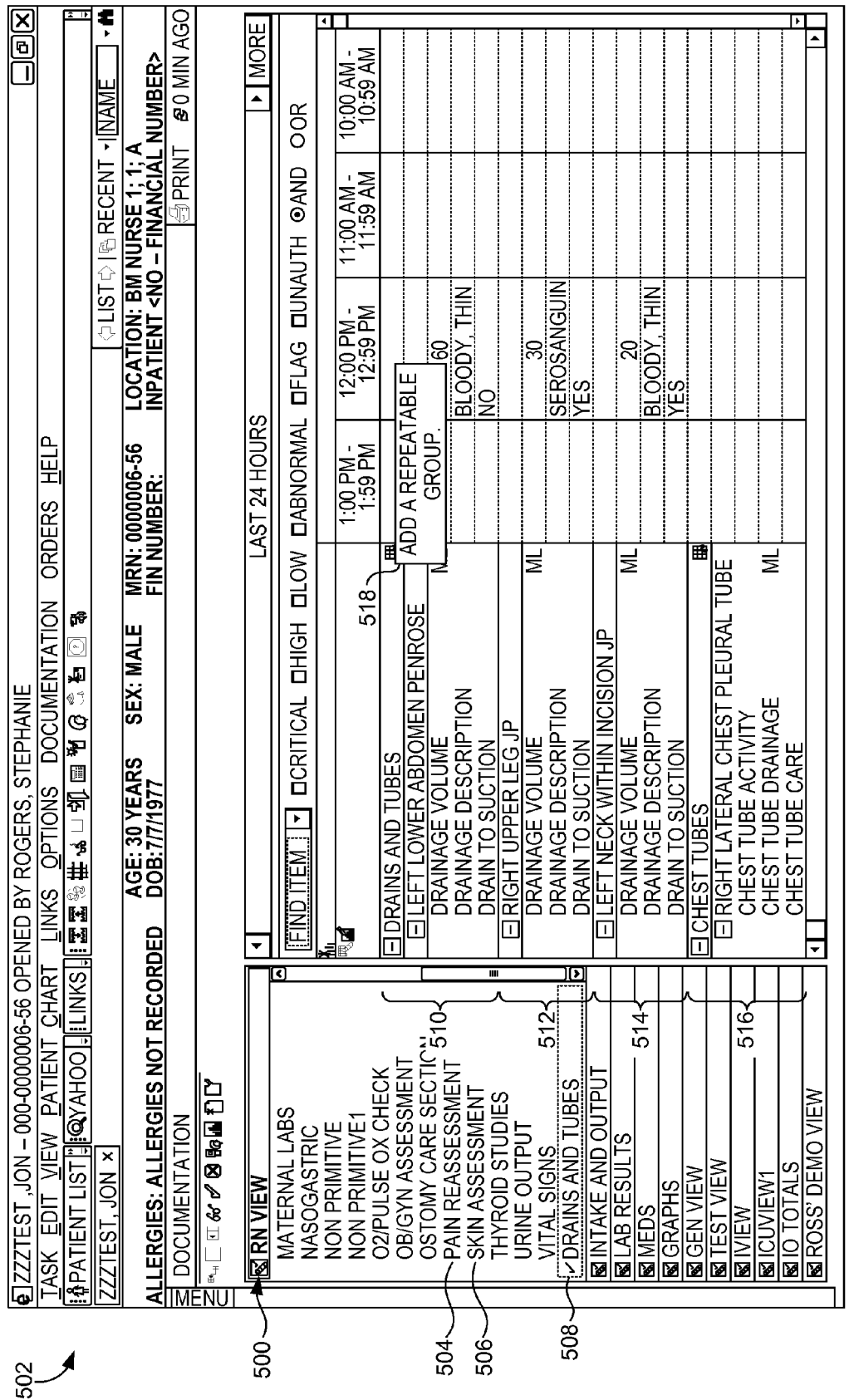
FIG. 5 is an illustrative screen display of an exemplary user interface for viewing medical documentation sets, in accordance with an embodiment of the present invention.

By way of illustration only, the exemplary displays of FIGS. 5-11 show views of screens displayed to a clinician in generating a medical documentation set within "RN View" of Cerner's Power Chart® application. With reference to FIG. 5, suppose, for instance, that a clinician accesses John ZZZ-Test's record within an RN View 500 of a medical documentation service 502. In accessing John ZZZTest's record within the RN View 500 of a medical documentation service 502, the clinician may view, among others items, a pain reassessment medical category 504, a skin assessment medical category 506, and a drains and tubes medical category 508. Suppose further that the clinician selects the medical category drains and tubes 508 as displayed in view 502 of FIG. 5. Upon selecting the drains and tubes medical category, various existing medical documentation sets 510, 512, 514, and 516 are presented. Further assume, that a medical template has, previously, been generated. As such, a medical template availability notice 518 is also presented.

Figure 6:
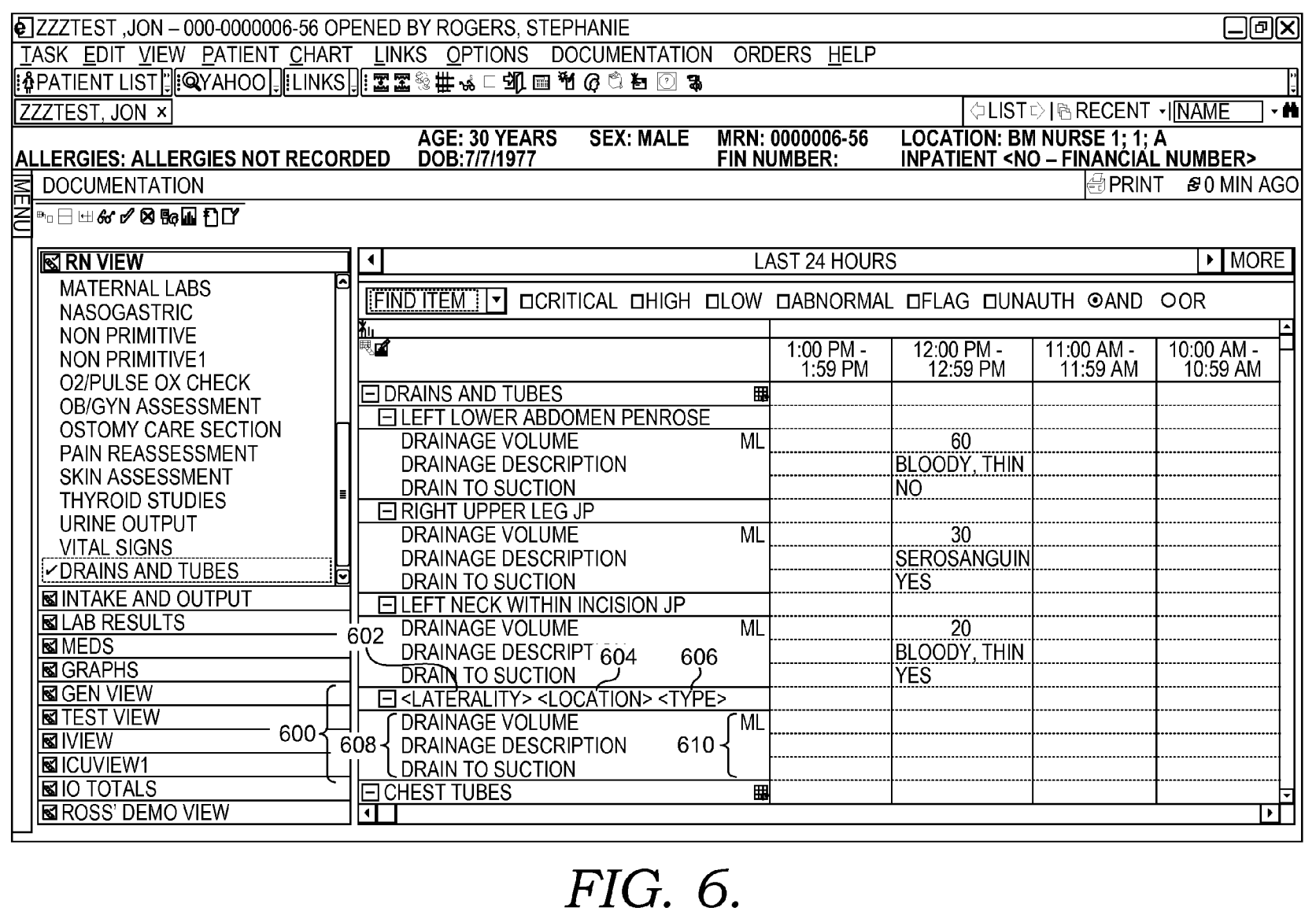

The clinician may select to indicate a desire to generate a medical documentation set by selecting medical template availability notice 518. Upon selection to generate a medical documentation set, such as clicking on medical template availability notice 518 of FIG. 5, the medical documentation set 600 of FIG. 6 is presented. The initial medical documentation set 600 of FIG. 6 includes a drain laterality label element 602, a drain location label element 604, a drain type label element 606, a set of documentation elements 608, and a set of medical data fields 610.

Figure 7:
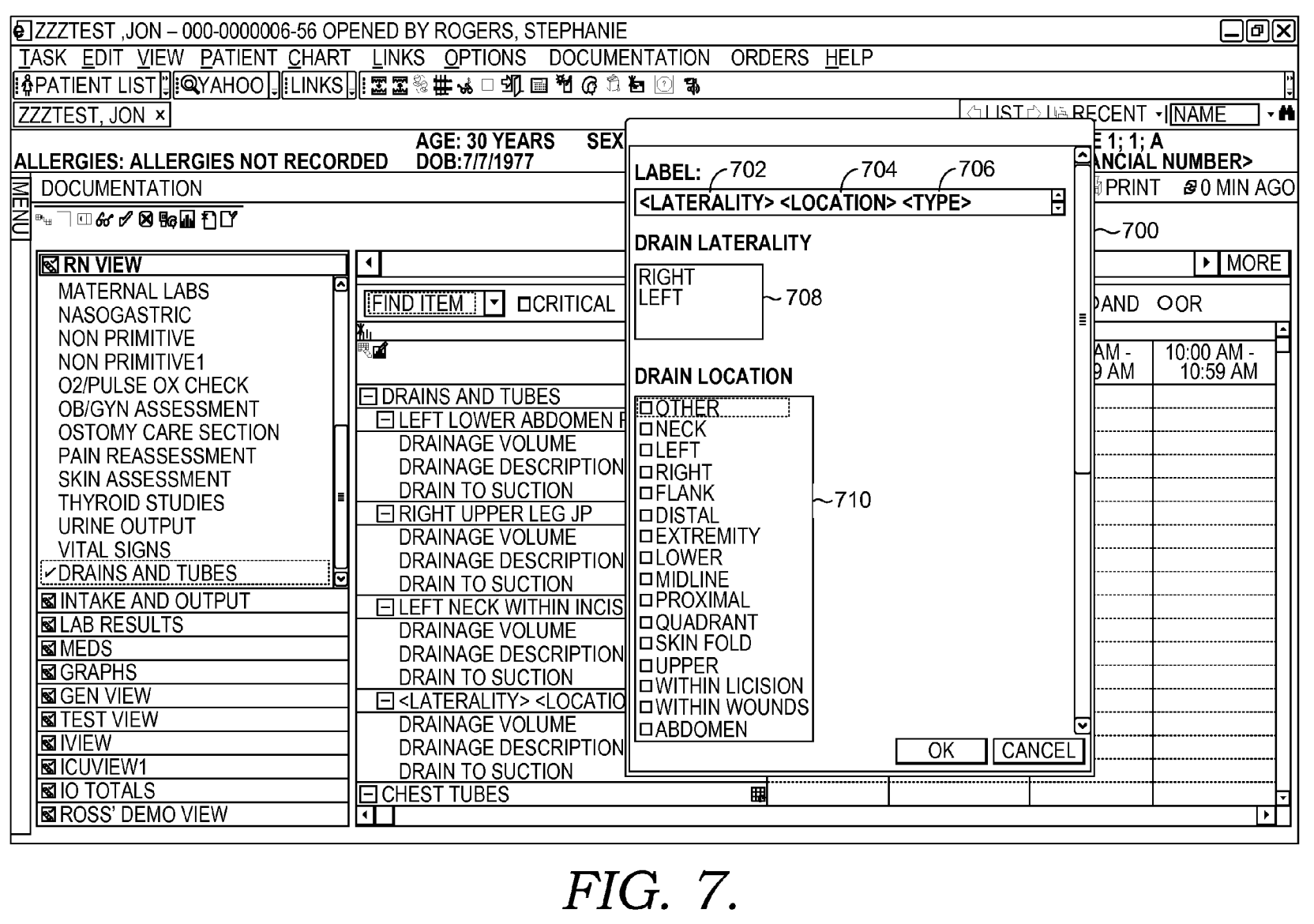

The clinician may select to provide a unique label for the medical documentation set 600. Upon such a selection, such as clicking on the medical label elements 602, 604, or 606 of FIG. 6, the document set labeling portion 700 of FIG. 7 is presented. The label elements 702, 704, and 706 are presented near the top of the document set labeling portion 700. The document set labeling portion 700 of FIG. 7 also presents descriptive terms 708 and 710 that may be utilized to replace the medical label elements, respectively. The clinician may select descriptive term right to replace medical label element 702 and descriptive term lower 804 and descriptive term abdomen 806 to replace medical label element 704. The unique label 808 for the medical documentation set 600 is presented.

Figure 9:
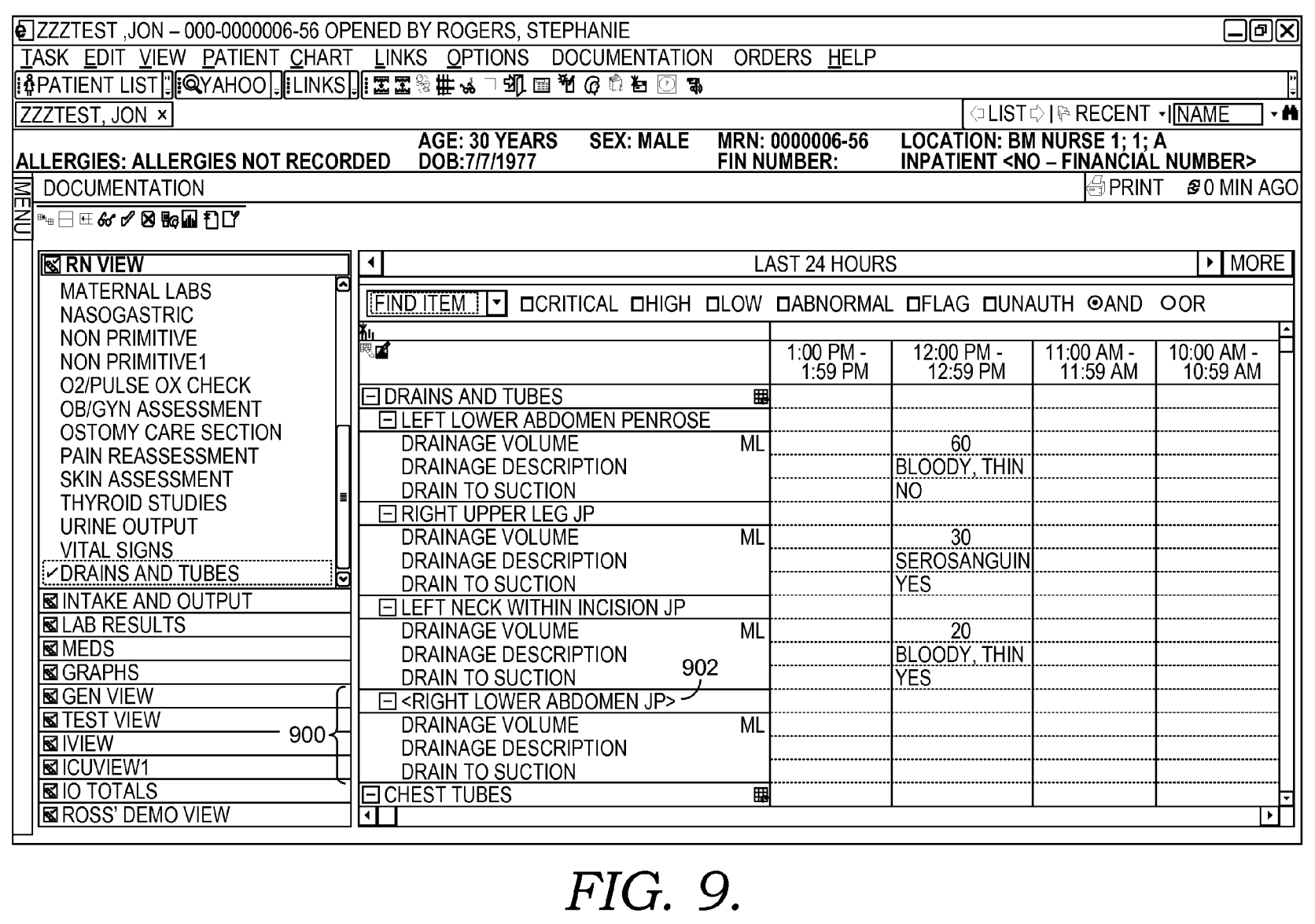

Upon selecting okay 810, the medical documentation set 900 of FIG. 9 is presented with the unique label 902. The clinician may enter medical data 1000 into medical data fields associated with the documentation elements 1002. The clinician may also select to provide a signature, such as clicking on the signature box 1004, for the medical label and/or medical data. Upon selecting to provide a signature, the medical documentation set 1100, including the unique medical label 1102 and the medical data 1104, is presented in a final form.

Figure 12:
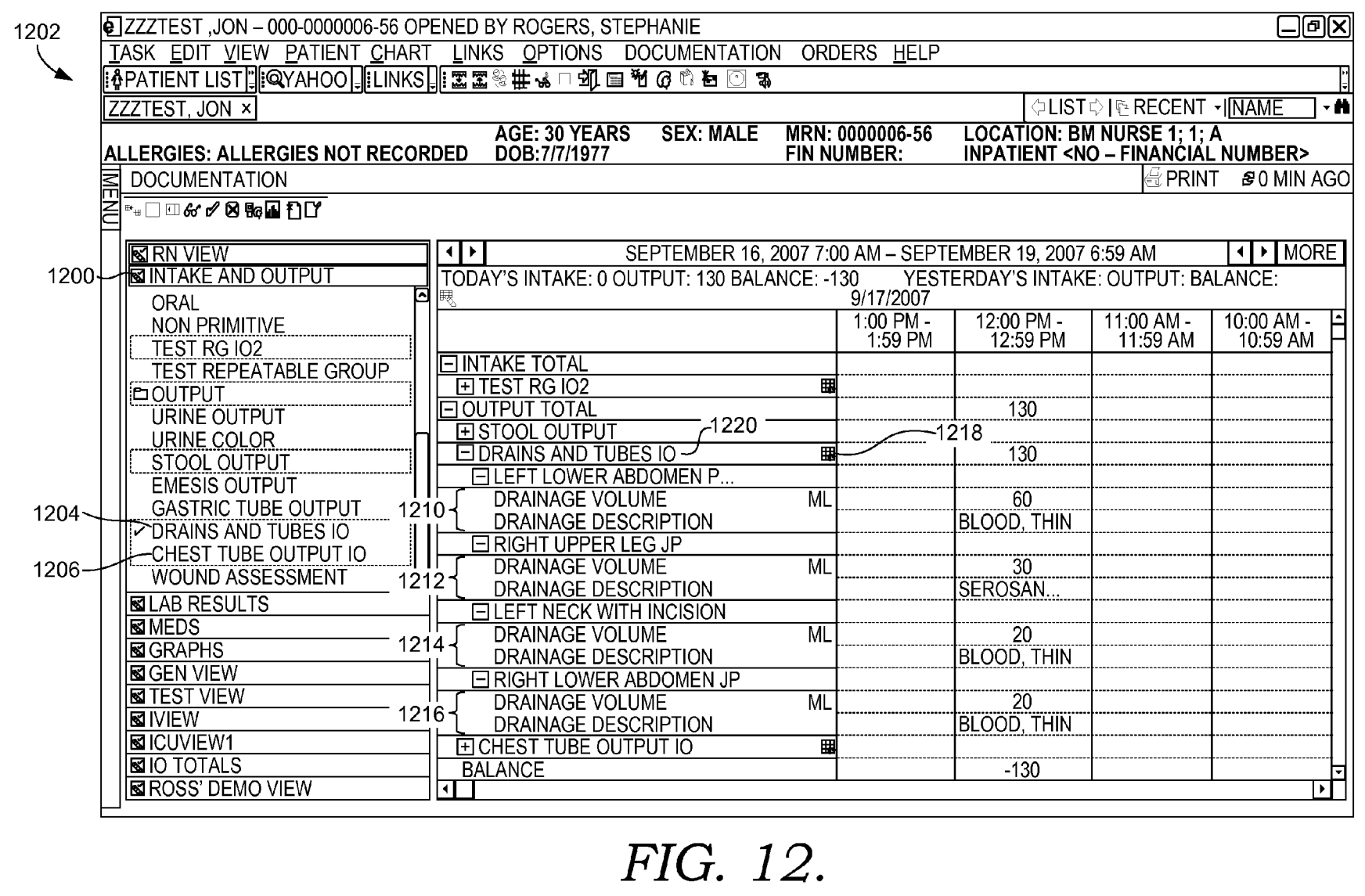

By way of illustration only, the exemplary displays of FIGS. 12-20 show views of screens displayed to a clinician in generating a medical documentation set within "Intake and Output View" of Cerner's Power Chart® application. With reference to FIG. 12, suppose, for instance, that a clinician accesses John ZZZTest's record within an Intake and Output View 1200 of a medical documentation service 1202. In accessing John ZZZTest's record within the Intake and Output View 1200 of a medical documentation service 1202, the clinician may view, among others items, a drains and tubes medical category 1204 and a chest tube output medical category 1206. Suppose further that the clinician selects the medical category drains and tubes medical category 1204, among other medical categories, as displayed in view 1202 of FIG. 12. Upon selecting the drains and tubes medical category, various existing medical documentation sets 1210, 1212, 1214, and 1216 are presented. Further assume, that a medical template has, previously, been generated. As such, a medical template availability notice 1218 is also presented adjacent to the drains and tubes medical category 1220.

The clinician may select to indicate a desire to generate a medical documentation set by selecting medical template availability notice 1218. Upon selection to generate a medical documentation set, such as clicking on medical template availability notice 1218 of FIG. 12, the medical documentation set 1300 of FIG. 13 is presented. The initial medical documentation set 1300 of FIG. 13 includes a drain laterality label element 1302, a drain location label element 1304, a set of documentation elements 1306, and a set of medical data fields 1308.

Figure 14:
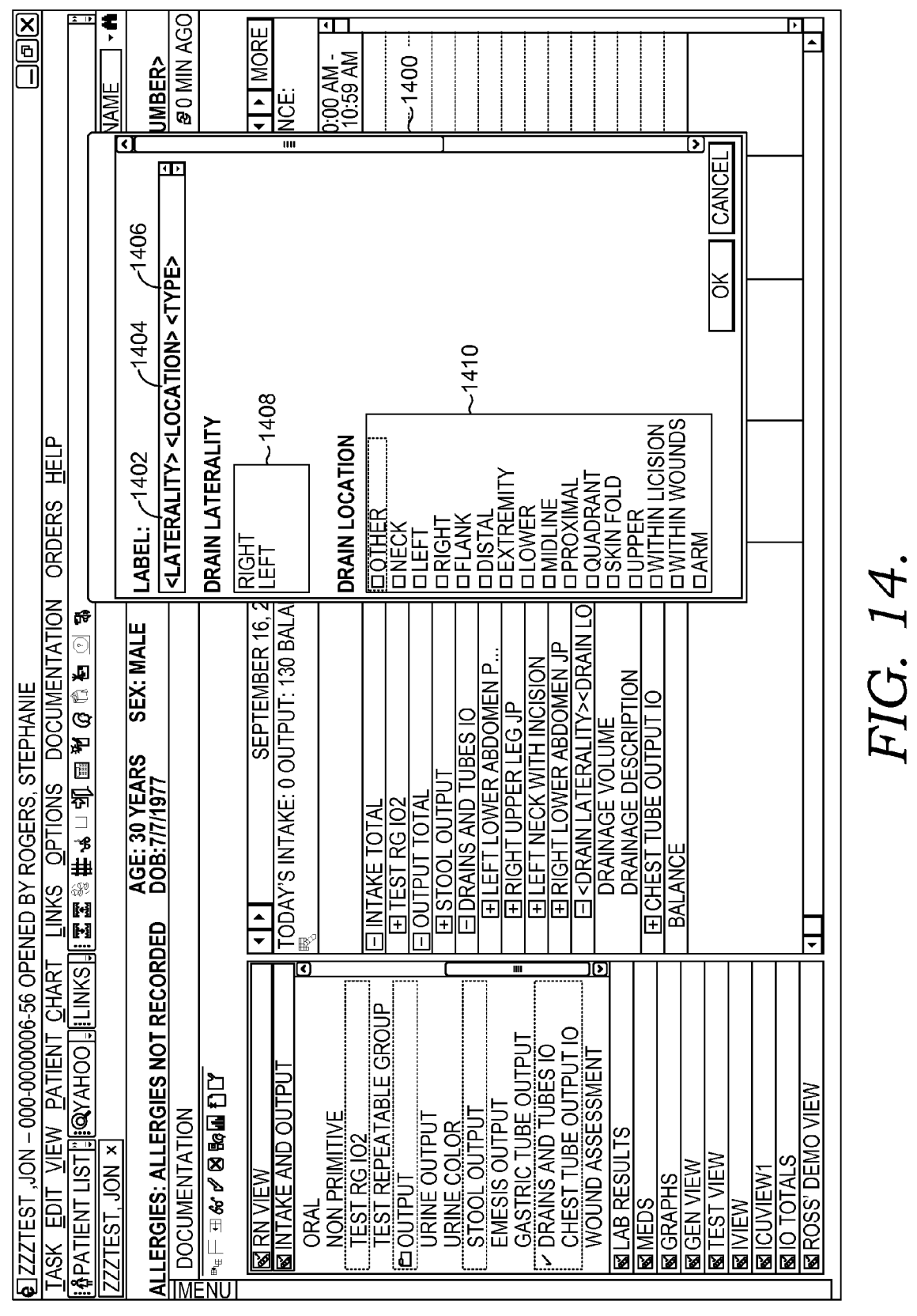

The clinician may select to provide a unique label for the medical documentation set 1300. Upon such a selection, such as clicking on the medical label elements 1302 or 1304 of FIG. 13, the document set labeling portion 1400 of FIG. 14 is presented. The label elements 1402, 1404, and 1406 are presented near the top of the document set labeling portion 1400. The document set labeling portion 1400 of FIG. 14 also presents descriptive terms 1408 and 1410 that may be utilized to replace the medical label elements 1402 and 1404, respectively. The clinician may select descriptive term left 1502 to replace medical label element 1402 and descriptive term arm 1504 to replace medical label element 1404. The unique label 1506 for the medical documentation set 1300 of FIG. 13 is presented.

Figure 16:
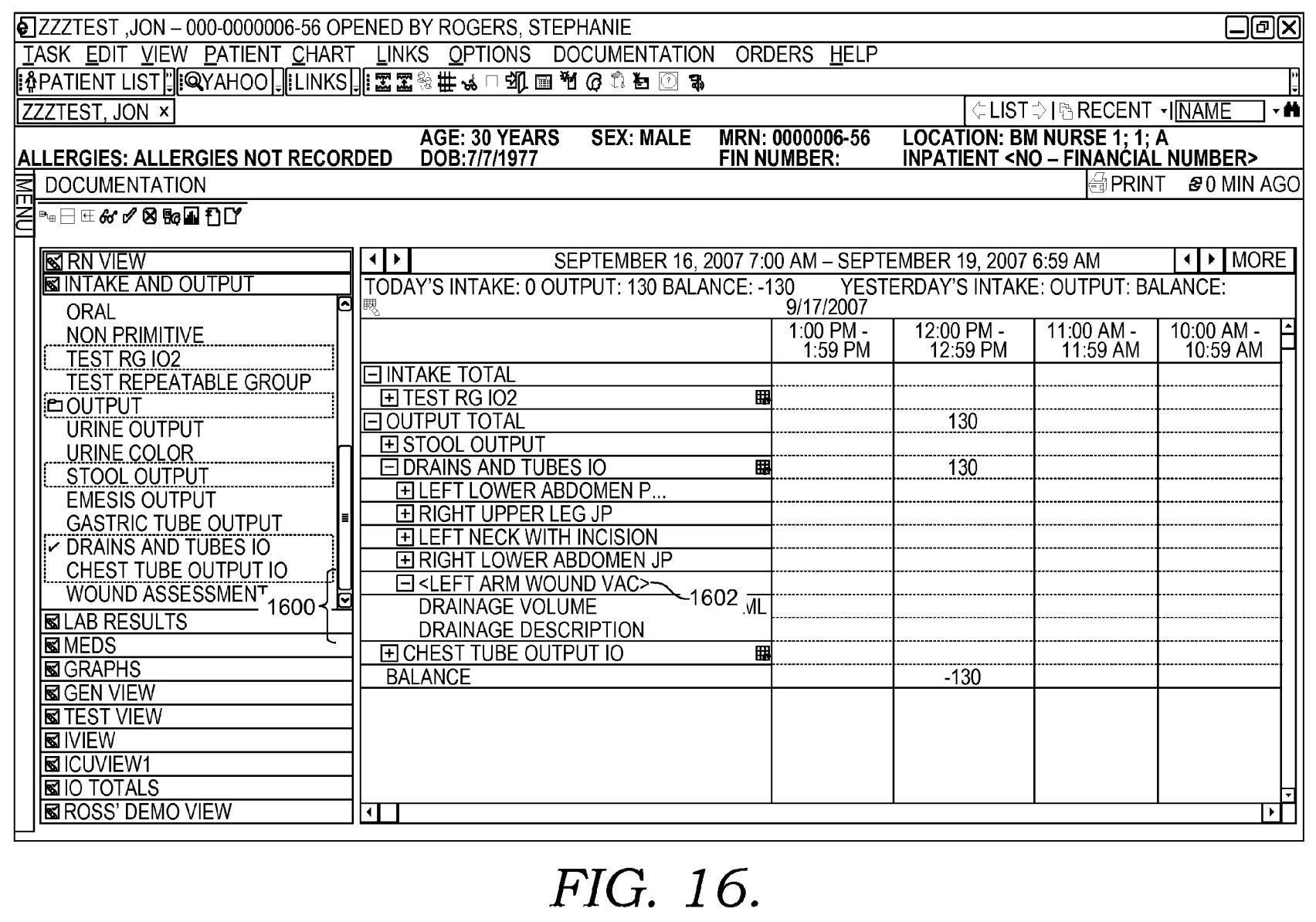
Figure 17:
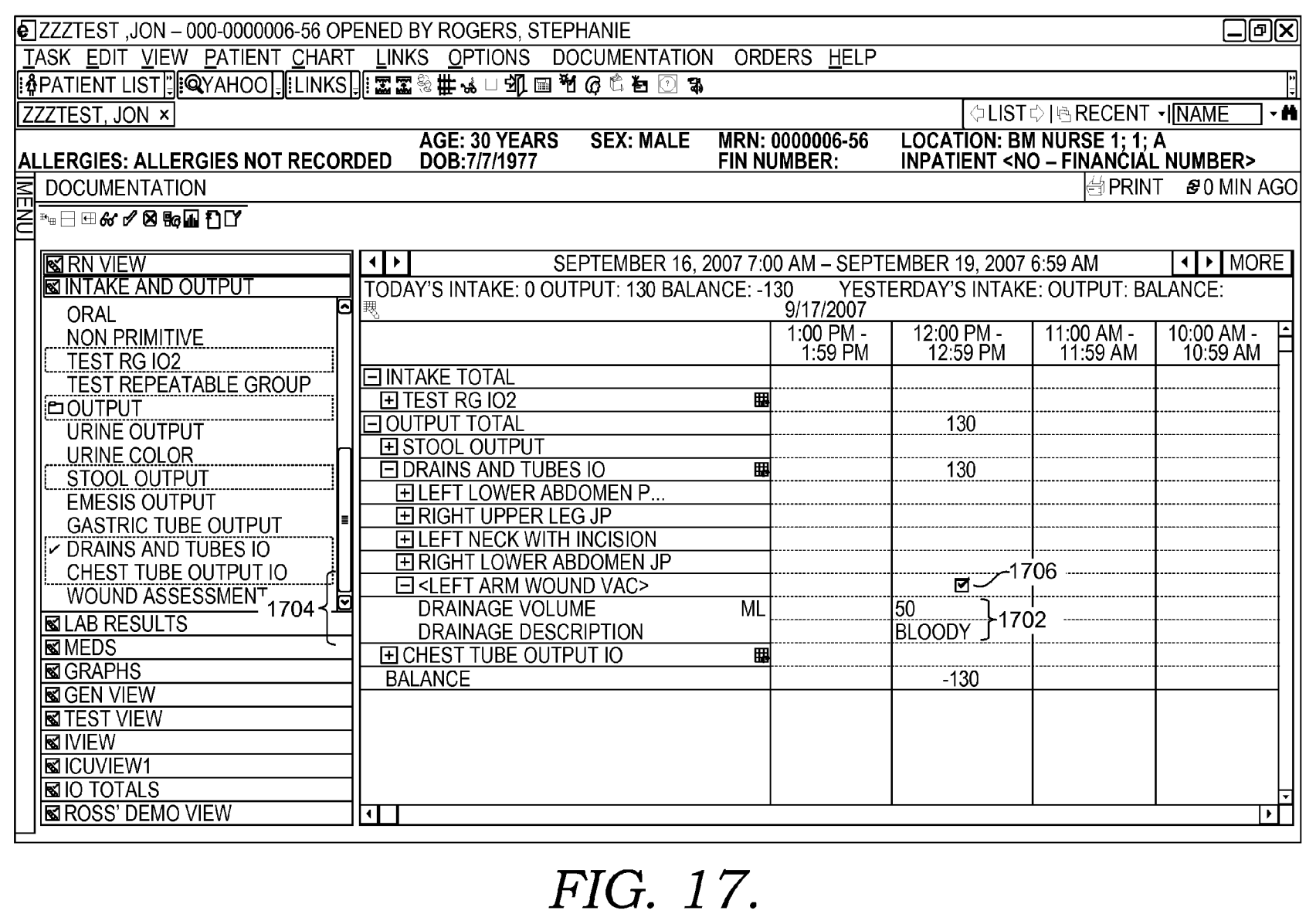
Figure 18:
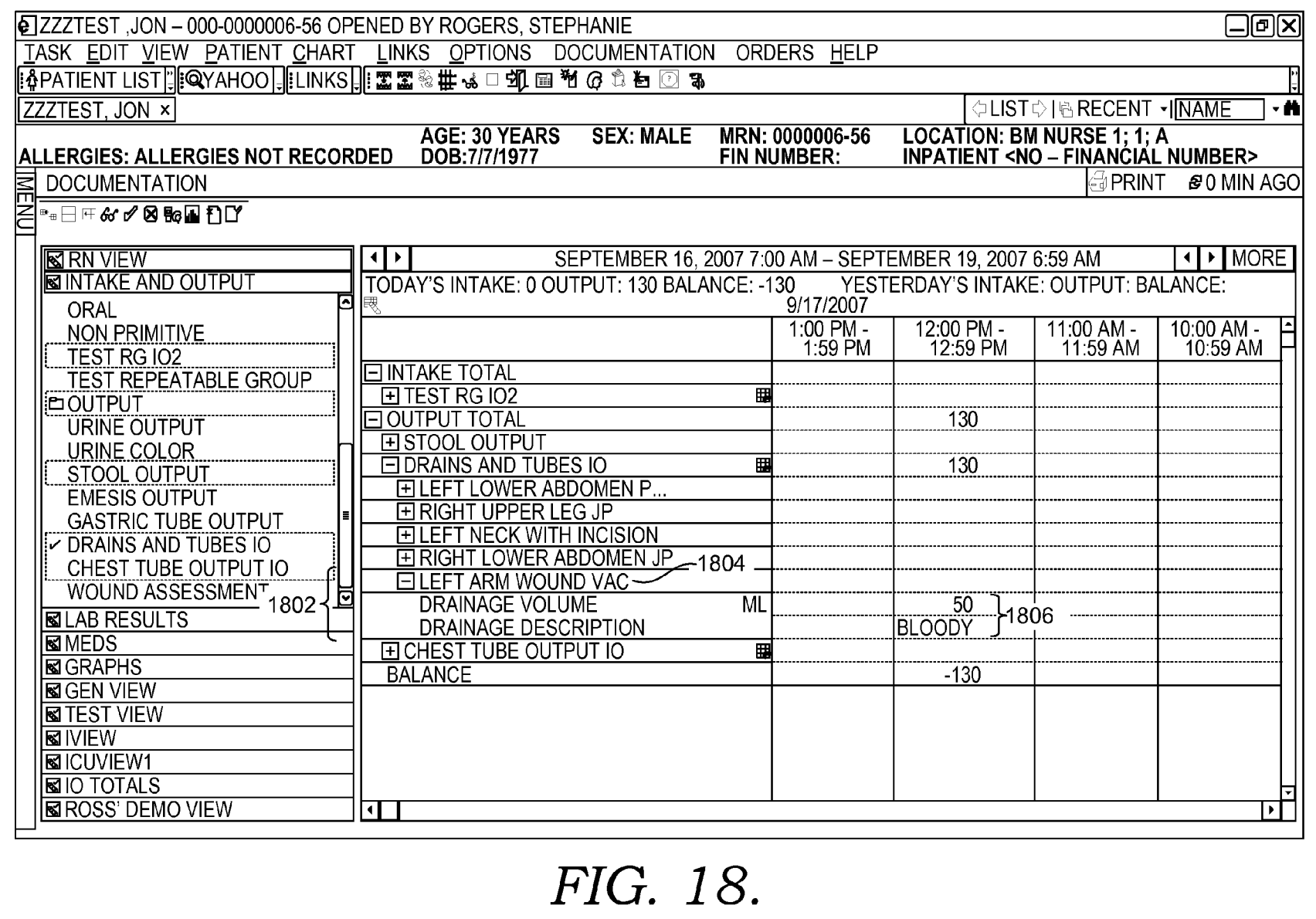

Upon selecting okay 1508, the medical documentation set 1600 of FIG. 16 is presented with the unique label 1602. The clinician may enter medical data 1702 of FIG. 17 into medical data fields associated with the documentation elements 1704. The clinician may also select to provide a signature, such as clicking on the signature box 1706, for the medical label and/or medical data. Upon selecting to provide a signature, the medical documentation set 1802, including the unique medical label 1804 and the medical data 1806, is presented in a final form. Assume that after generating the medical documentation set 1802 of FIG. 18, the clinician desires to utilize the RN View. Upon selecting the RN View 1900 of FIG. 19 and the drains and tubes medical category 1902, the clinician is presented with the medical documentation set 1904 within the RN View.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated and within the scope of the claims.

What is claimed is:

1. A method for generating medical documentation sets, the method comprising:
   receiving an indication to present a medical documentation set that corresponds with a medical category;
   utilizing a medical template associated with the medical category to present the medical documentation set within a first documentation view, the medical documentation set comprising:
      a medical label comprising one or more medical label elements, wherein each of the one or more medical label elements indicates a category of label terms to use to generate a unique medical label for the medical documentation set,
      a set of one or more medical documentation elements that indicate a medical aspect for which medical data is to be documented, and
      a set of medical data fields for receiving input of the medical data associated with care provided to a patient at a point of care;
   receiving, via a computing device, an indication of a label term within each of the categories of label terms to replace the corresponding medical label element by sequentially receiving a selection of the label term from a list of label terms that are presented on the documentation view for each of the categories of label terms;
   generating the unique medical label that uniquely identifies the medical documentation set by replacing each of the medical label elements with the corresponding selected label term, the unique medical label comprising a combination of the selected label terms that medically describes care associated with the patient; and
   capturing the medical documentation set.

2. The method of claim 1 further comprising receiving a selection of the medical category.

3. The method of claim 1 further comprising generating the medical template.

4. The method of claim 3, wherein generating the medical template comprises:
   receiving an indication of the medical category to which the medical template corresponds;

receiving an indication of the one or more medical label elements to include within the medical label of the medical template;
receiving an indication of the set of medical documentation elements to include within the medical template; and
aggregating the one or more medical label elements and the set of medical documentation elements to generate the medical template.

5. The method of claim 1 further comprising presenting a set of label terms for replacing the one or more medical label elements.

6. The method of claim 1 further comprising receiving medical data within the medical data fields, wherein the medical data is documented at a point of care in association with medical care provided to the patient.

7. The method of claim 6 further comprising automatically determining if the received medical data matches a predetermined attribute and, if so, providing at least one additional medical data field.

8. The method of claim 7 further comprising presenting the medical documentation set within the medical category of a second documentation view.

9. The method of claim 8 further comprising presenting a graph representing data documented within a plurality of medical documentation sets, wherein the data is associated with a specific medical documentation element.

10. A computerized system in a clinical environment for generating medical documentation sets, the system comprising:
a processing unit; and
a memory for storing computer-executable instructions that when executed by the processing unit executes:
a generation indicating component configured to receive an indication to generate a medical documentation set;
a documentation set presenting component configured to present the medical documentation set in accordance with a medical template that includes a set of medical label elements for indicating a group of label terms to use to describe care provided to a patient, a set of medical documentation elements that indicate a medical aspect corresponding to the medical category for which medical data is to be documented; and a set of medical data fields for initially documenting the medical data associated with the care provided to the patient;
a documentation set labeling component configured to receive an indication of a label term from each group of label terms to replace the corresponding medical label element by receiving a selection of the label term from a list of label terms that are presented for each of the groups of label terms, and to generate a unique medical label that uniquely designates the medical documentation set by replacing each of the medical label elements with the corresponding selected label term, the unique medical label comprising a combination of the selected label terms that medically describes care provided to the patient; and
a capturing component for saving the medical documentation set.

11. The computerized system of claim 10 further comprising a documentation receiving component configured to receive medical data associated with the patient care, wherein the medical data is documented at the point of care.

12. The computerized system of claim 10 further comprising an availability notice presenting component configured to present a medical template availability notice to indicate that the medical template is available to use to generate the medical documentation set.

13. The computerized system of claim 10 further comprising a medical template generation module configured to generate the medical template.

14. The computerized system of claim 13, wherein the medical template generation module comprises:
a template generator presenting component configured to present a medical template generator tool for use by a user to generate the medical template;
an obtaining component configured to obtain the medical category in association with the medical template, the set of medical label elements, and the set of medical documentation elements; and
a template formatting component configured to format the medical template using the set of medical label elements and the set of medical documentation elements.

15. The computerized system of claim 14, wherein the medical template is saved.

16. The computerized system of claim 15, wherein a medical template name is assigned to the medical template.

17. One or more computer storage media having computer-executable instructions embodied thereon for performing a method for generating medical documentation sets, the method comprising:
receiving an indication to generate a medical documentation set for a medical category, wherein the medical documentation set comprises one or more first medical label elements, one or more first medical documentation elements, and one or more first medical data fields;
presenting the medical documentation set among at least one other medical documentation set within the medical category of a first documentation view such that the first documentation view displays the medical documentation set including the one or more first medical label elements, the one or more first medical documentation elements, and the one or more first medical data fields and the at least one other medical documentation set including one or more second medical label elements, one or more second medical documentation elements, and one or more second medical data fields within the first documentation view;
receiving an initial text input of one or more first medical data associated with care provided to a patient at a point of care within the one or more first medical data fields, wherein when at least one of the one or more first medical data within the one or more first medical data fields comprises a predetermined attribute that is a specific text, value, value range, or symbol, providing one or more third medical documentation elements and one or more third medical data fields that correspond with the one or more third medical documentation elements;
receiving an indication of a label term from each category of label terms to replace a corresponding first medical label element by receiving a selection of the label term from a list of label terms that are presented for each of the categories of label terms;
replacing each of the first medical label elements with the corresponding selected label term to generate a unique medical label that uniquely identifies the medical documentation set, the unique medical label comprising a combination of the selected label terms that medically describes care associated with the patient; and
capturing the medical documentation set.

18. The one or more computer storage media of claim 17 further comprising generating the medical template to use to generate the medical documentation set.

19. The one or more computer storage media of claim 17 further comprising presenting the medical documentation set within the medical category of a second documentation view.

20. The one or more computer storage media of claim 17 further comprising presenting a graph representing data documented within a plurality of medical documentation sets, wherein the data is associated with a specific documentation element.

* * * * *